United States Patent [19]

Roeschert et al.

[11] Patent Number: 5,191,069
[45] Date of Patent: Mar. 2, 1993

[54] POLYFUNCTIONAL COMPOUNDS CONTAINING α-DIAZO-β-KETO ESTER UNITS AND SULFONATE UNITS

[75] Inventors: Horst Roeschert, Ober-Hilbersheim; Georg Pawlowski, Wiesbaden; Hans-Joachim Merrem, Basking Ridge; Ralph Dammel, Klein-Winternheim, all of Fed. Rep. of Germany

[73] Assignee: Hoechst Aktiengesellschaft, Frankfurt am Main, Fed. Rep. of Germany

[21] Appl. No.: 694,386

[22] Filed: May 1, 1991

[30] Foreign Application Priority Data

May 8, 1990 [DE] Fed. Rep. of Germany ....... 4014649

[51] Int. Cl.$^5$ ................ C07C 245/18; C07C 245/14; C07F 5/02; C07F 7/18
[52] U.S. Cl. ..................... 534/556; 534/557; 534/565; 534/561; 534/560
[58] Field of Search ............... 534/556, 557, 565, 561, 534/560

[56] References Cited

U.S. PATENT DOCUMENTS

| | | | |
|---|---|---|---|
| 4,339,522 | 7/1982 | Balanson et al. | 430/192 |
| 4,556,513 | 12/1985 | Shibahara et al. | 534/556 X |
| 4,622,283 | 11/1986 | Gray | 430/191 |
| 4,735,885 | 4/1986 | Hopf et al. | 430/192 |
| 4,939,241 | 7/1990 | Okuhara et al. | 534/556 |
| 4,996,301 | 2/1991 | Wilharm et al. | 534/556 |

FOREIGN PATENT DOCUMENTS

| | | | |
|---|---|---|---|
| 0195986 | 10/1986 | European Pat. Off. | 534/556 |
| 0198674 | 10/1986 | European Pat. Off. | 430/192 |
| 0319325 | 6/1989 | European Pat. Off. | 534/556 |
| 3841571A1 | 6/1989 | Fed. Rep. of Germany | 534/556 |
| 1-265066 | 10/1989 | Japan | 534/556 |
| 2173801 | 10/1986 | United Kingdom | 534/556 |

OTHER PUBLICATIONS

(Endo et al.) Chemical Abstracts, vol. 111, 1989, 111:222146b—JP 01,106,034, Positive-Working Photoresist Material for Fine Patterning, etc.
Chemical Abstracts, vol. 99, 1983, 99:53746y Bicyclic Diazodiketo–Cyclopentanes, SU-1,004,359, (Korobitsyna et al.).
Chemical Abstracts, vol. 111, 1989, 111:123850v, Photosensitive Resin Compositions for Fine Patterning, JP 0180,944 (Sugyama et al.).
Chemical Abstracts, vol. 111, 1989, 111: 15357f Positive-Working Photoresist, JP 63,253,938 (Endo et al.).
(Endo et al.) Chemical Abstracts, vol. 111, 1989, 111:221148d Positive-Working Photoresist Material for Fine, etc. JP 01,106,036.
(Endo et al.) Chemical Abstracts, vol. 111, 1989, 111:48157v Photoresist Compositions, JP 01,10,237.
Proceedings of SPIE-vol. 771, "Advances in Resist Technology and Processing IV". Mar. 2–3, 1987, Murrae J. Bowden.
H. Sugiyama, K. Ebata, A. Mizushima and K. Nate, "Positive Excimer Resist Prepared with Aliphatic Diazoketones in SPIE", 920 1988.
Patent Abstracts of Japan, 13, Nr. 478 (P-951) [3826], 30, Oct. 1989 & JP-A-1 188 852 (Matsushita Electric Ind. Co., Ltd), Jul. 28, 1989.

*Primary Examiner*—Floyd D. Higel
*Attorney, Agent, or Firm*—Foley & Lardner

[57] ABSTRACT

Polyfunctional compounds containing α-diazo-β-keto ester units and sulfonate units are disclosed. The polyfunctional compounds have high sensitivity in the deep UV and high thermal stability. Processes for producing the compounds are disclosed. A preferred process first synthesizes β-ketoester/sulfonate precursors and then uses diazo transfer to convert the precursors into the novel compounds. Radiation-sensitive mixtures containing the compounds are also disclosed.

42 Claims, No Drawings

POLYFUNCTIONAL COMPOUNDS CONTAINING α-DIAZO-β-KETO ESTER UNITS AND SULFONATE UNITS

BACKGROUND OF THE INVENTION

The invention relates to novel polyfunctional compounds containing α-diazo-β-keto ester units and sulfonate units, to a process for their preparation, and to their use as photoactive components in radiation-sensitive mixtures.

Radiation-sensitive mixtures containing photoactive diazo derivatives which are suitable for irradiation with high-energy UV radiation have been described in the literature for some time.

U.S. Pat. No. 4,339,522 discloses positive-working radiation-sensitive mixtures which contain, as a photoactive compound, a diazo derivative of Meldrum's acid. This compound is said to be suitable for exposure to high-energy UV radiation in the range between 200 and 300 nm. On the use of these mixtures, however, it became apparent that the photoactive compound is exuded under the elevated processing temperatures frequently employed in practice; the radiation-sensitive mixture loses its original activity, so that reproducible structuring is not possible.

EP-A 0 198 674 and 0 262 864, JP-A 01/106 034, U.S. Pat. No. 4,622,283 and SU-A 1 004 359 provide 2-diazocyclohexane-1,3-dione or -cyclopentane-1,3-dione derivatives as photoactive compounds for radiation-sensitive mixtures of the type described. These compounds have lower volatility, but this is balanced by the fact that they exhibit, depending on the substitution pattern present, poor compatibility in the radiation-sensitive mixture. This becomes apparent, in particular, on drying of the coatings by the photoactive compound crystallizing out, by their insolubility in solvents which are suitable in practice or by coating inhomogeneity caused by phase separation.

Further positive-working photoactive compounds which are sensitive in the deep UV region are disclosed in EP-A 0 129 694 and U.S. Pat. No. 4,735,885. The compounds described in these documents have the disadvantage that the carbenes formed from these on exposure do not have adequate stability in the matrix for the desired formation of carboxylic acid. This results in an inadequate solubility difference between the exposed and unexposed areas in the developer and thus in an undesirably high removal rate of the unexposed areas. A possible explanation for this phenomenon is given by C.G. Willson et al. in SPIE, Vol. 771, "Advances in Resist Technology and Processing IV", 2 (1987).

EP-A 0 195 986 therefore proposes α-phosphoryl-substituted diazocarbonyl compounds as photoactive compounds, since these have a higher carbene stability. In practice, however, such compounds will probably not be widely used since atoms of potential use for doping, such as, for example, the phosphorus present in these compounds, must be excluded with extreme care in the processing operations.

H. Sugiyama, K. Ebata, A. Mizushima and K. Nate in their paper "Positive Excimer Laser Resist Prepared with Aliphatic Diazoketones" [SPIE Proc., 920, 51 (1988)], present novel α-diazoacetoacetates which are employed as photoactive compounds in positive-working radiation-sensitive mixtures, in particular on use of radiation in the deep UV range. Since these are derivatives of acetoacetic acid, the keto group in the β-position to the ester group is directly adjacent to a terminal methyl group.

Diazo derivatives of acetoacetic acid are also employed in EP-A 0 319 325 and DE-A 38 41 571 as radiation-sensitive components in the deep UV range (<300 nm). Radiation-sensitive mixtures which contain the said compounds as photoactive components have good bleaching properties, but their properties with respect to image differentiation are poor.

Aliphatic bis(carbonyl)diazomethanes, which are used in JP-A 01/080 944, have inadequate thermal stability, which is why such compounds are hardly used at all in practice. For bis(carbonyl)diazomethanes, which are claimed in JP-A 63/253 938, 01/106 036 and 01/010 237, the same applies as for the derivatives of acetoacetic acid.

SUMMARY OF THE INVENTION

Accordingly, it is an object of the present invention to provide photoactive compounds which avoid the numerous disadvantages described above.

Another object of the present invention is to provide photoactive compounds which have high sensitivity in the deep UV and give, in particular as components in radiation-sensitive mixtures, coatings which allow good differentiation between the exposed and unexposed areas of the coating.

A further object of the present invention is to provide photoactive compounds which are readily compatible with a wide range of polymers used in practice, do not exude from the radiation-sensitive mixture, and have high thermal stability and practical photosensitivity.

Yet another object of the present invention is to provide a method for producing the foregoing photoactive compounds.

In accomplishing the foregoing objectives, there has been provided, in accordance with one aspect of the present invention, a polyfunctional compound comprising α-diazo-β-keto ester units and sulfonate units, of the general formula I

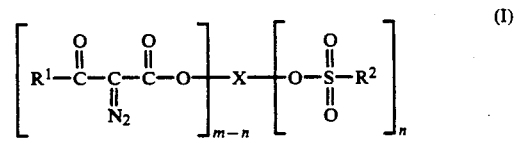

in which
R$^1$ and R$^2$, independently of one another, are an unsubstituted or substituted aliphatic, cycloaliphatic, araliphatic or aromatic radical having 4 to 20 carbon atoms, it being possible for individual CH$_2$ groups to be replaced by oxygen or sulfur atoms or by N or NH groups and/or contain keto groups,
X is an unsubstituted or substituted aliphatic, cycloaliphatic, carbocyclic, heterocyclic or araliphatic radical having 2 to 22 carbon atoms, it being possible for individual CH$_2$ groups to be replaced by oxygen or sulfur atoms or by the groups —NR$^3$—, —C(O)—O—, —C(O)—NR$^3$—,

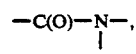

—NR$^3$—C(O)—NR$^4$—, —O—C(O)—NR$^3$—,

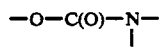

or —O—C(O)—O—, or CH groups to be replaced by

in which
R³ and R⁴, independently of one another, are hydrogen or an unsubstituted or substituted aliphatic, carbocyclic or araliphatic radical,
m is an integer from 3 to 8,
n is an integer from 1 to 3, and m>n.

In accordance with another aspect of the present invention, there is provided a process for preparing a polyfunctional compound as described above, comprising the steps of: dissolving a β-ketoester/sulfonate according to the formula II

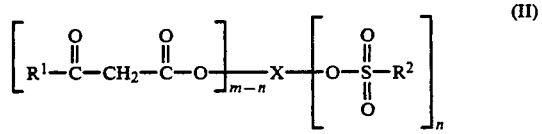

in which R¹, R² and X are as defined above, in from about 5 to 50 times of a solvent, based on the amount of said β-ketoester/sulfonate; reacting the β-ketoester/sulfonate with about a 1- to 1.3-fold excess, based on the number of activated methylene groups to be reacted, of a diazo transfer agent, and with a base; freeing the resultant reaction mixture from excess reagents and solvents; taking up the reaction mixture in a water-immiscible solvent; washing the resultant solution with a potassium hydroxide solution and subsequently with water until neutral; drying the neutral solution using a dessicant; and isolating the α-diazo-β-ketoester/sulfonate. In a preferred embodiment, the β-ketoester/sulfonate is first reacted with about a 0.7- to 0.9-fold excess of the diazo transfer agent, together with the entire amount of the base, and subsequently with about a 0.6- to 0.1-fold excess of the diazo transfer agent, to give the total excess of the diazo transfer agent.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

In a preferred embodiment, R³ and R⁴ are hydrogen, $(C_1-C_3)$alkyl, $(C_6-C_{12})$aryl or $(C_6-C_{11})$aralkyl, it likewise being possible for the radicals (in particular aryl or aralkyl) to be substituted on the ring by $(C_1-C_3)$alkyl, $(C_1-C_3)$alkoxy, halogen, in particular chlorine or bromine, or amino, in particular a primary or secondary amine. R³ and R⁴ are particularly preferably hydrogen or $(C_1-C_3)$alkyl, but in particular hydrogen.

The radicals R¹, R² and X may, if desired, be substituted, in particular by $(C_1-C_3)$alkyl, $(C_1-C_3)$alkoxy, halogen, in particular chlorine or bromine, nitrile, amino or nitro. Preferred radicals R¹, R² and X are those which are substituted by $(C_1-C_3)$alkyl or $(C_1-C_3)$alkoxy. In particular when R¹ and X are alkyl or alkylene, the unsubstituted derivatives are preferred. If R² is alkyl, by contrast, the substituted derivatives are preferred.

The aliphatic radicals R¹ may be straight-chain or branched. The number of chain members here is preferably from 4 to 10, in particular from 4 to 8. These include the particularly preferred pure carbon chains and the substituted chains in which $CH_2$ groups are replaced by oxygen atoms or —NH— groups and/or keto groups are present, which are also taken to mean ether, keto, ester, amido or imido groups, i.e. also esters of carbamic acid. Of the substituted aliphatic radicals R¹ those are particularly preferred in which methylene groups, especially 2 methylene groups, are replaced by oxygen atoms and which do not contain further substituents. If R¹ is a pure, in particular straight-chain, carbon chain, there is no necessity to limit the number of carbons; it is entirely possible for aliphatic radicals having up to 20 carbon atoms to be used. Nevertheless, the t-butyl radical is particularly preferred.

If R¹ is a cycloaliphatic radical, the number of ring members is preferably 4, 5, 6 or 12, in particular 4, 5 or 6. The unsubstituted variants are particularly preferred. Examples are the cyclobutyl, cyclopentyl and cyclohexyl radicals. The cyclohexyl radical is particularly preferred.

If R¹ is an araliphatic radical, the number of members of the aliphatic moiety of the radical is from 2 to 11, in particular from 2 to 5. If the aliphatic part is a pure carbon chain, the number of carbon atoms is preferably 1 or 2. If $CH_2$ groups are replaced by oxygen atoms, these may occur as bridging members between aromatic and aliphatic moieties of the radical R¹, but also in the aliphatic moiety itself. In both cases, it is particularly preferred for the total remaining number of carbon atoms as chain members in the aliphatic moiety of this radical to be 1 or 2, the ether oxygen atom in the case of 2 carbon atoms as chain members being arranged in such a manner that it is directly adjacent to the two $CH_2$ groups. Specific examples of araliphatic radicals are the benzyl, phenoxymethyl and benzyloxymethyl radicals. If, in addition, further $CH_2$ groups in the aliphatic moiety of the araliphatic radical R¹ are replaced by heteroatoms and/or this moiety is substituted, the total number of chain members of the aliphatic moiety is from 3 to 5. This includes, inter alia, phenyl or benzyl radicals bonded via ester groups, but also benzyl or phenyl esters of carbamic acid. However, the aliphatic moiety may also be the imido group of an aromatic dicarboxylic acid. The aromatic moiety of a radical of this type comprises, in particular, 6 carbon atoms. If the aromatic moiety of the araliphatic radical is bonded directly adjacent to the keto group, i.e. as an arylene radical, there are no limitations for the aliphatic moiety present therein with respect to the minimum number of carbon atoms present.

The aromatic radicals R¹ preferably contain no heteroatoms, such as, for example, oxygen in the ring system. If R¹ is an aromatic radical, it preferably contains 6 to 12 carbon atoms, in particular 6 carbon atoms, i.e. it is a phenyl radical. However, aromatic radicals R¹ are generally not preferred.

Overall, particularly preferred radicals R¹ are t-butyl, n-hexyl, nonyl, octadecyl, 2,5-dioxahexyl, cyclopentyl, cyclohexyl, benzyl, phenoxymethyl and benzyloxymethyl. The t-butyl, phenoxymethyl and cyclohexyl radicals are especially preferred.

The aliphatic radicals R² may be straight-chain or branched. The number of chain members here is preferably from 1 to 8, in particular from 2 to 6. These include both pure carbon chains and substituted chains in which CH₂ groups have been replaced by oxygen atoms or —NH— groups and/or contain keto groups, including ether, keto, ester, amido or imido groups. In the pure aliphatic radicals R², branched carbon chains are preferred. There is no necessity to limit the number of carbon atoms; it is entirely possible for aliphatic radicals having more than 8 carbon atoms to occur. Nevertheless, the i-propyl and the t-butyl radicals are preferred.

If R² is a cycloaliphatic radical, the number of ring members is preferably 4, 5, 6 or 12, in particular 5 or 6. The unsubstituted variants are preferred. However, cycloaliphatic radicals R² are overall not preferred.

If R² is an araliphatic radical, the number of members of the aliphatic moiety is from 2 to 11, in particular from 2 to 5. If the araliphatic radical is a pure carbon chain, the number of carbon atoms is preferably 1. If CH₂ groups are replaced by oxygen atoms, they may occur as bridging members between the aromatic and aliphatic moieties of the radical R², but also in the aliphatic moiety. In both cases, it is particularly preferred for the total remaining number of carbon atoms as chain members in the aliphatic moiety of this radical to be 1 or 2. The aromatic moiety of the araliphatic radical R² comprises in particular 6 carbon atoms.

The aromatic radicals R² may contain heteroatoms, such as sulfur or oxygen, in their ring system. These are preferably substituted. If R² is an aromatic radical, it preferably contains 6 to 12 carbon atoms, in particular 6 carbon atoms, i.e. it is a phenyl radical. Aromatic radicals R² are particularly preferred. If the aromatic radicals R² are substituted, they are preferably alkyl, alkoxy, halogen, nitrile or nitro groups. However, amino and amido groups are also possible as substituents. There are no limitations with respect to the number of substituents and the substitution pattern.

Overall, particularly preferred radicals R² are lower alkyl radicals (C₁–C₄), such as i-propyl and t-butyl, which may, if desired, be substituted by halogen atoms, and aromatic compounds. Phenyl radicals which are substituted in the 4-position by methyl, t-butyl, trifluoromethyl, bromine or cyano groups are especially preferred.

X is an aliphatic or cycloaliphatic radical, which may be saturated or unsaturated, or a carbocyclic, heterocyclic or araliphatic radical having 2 to 22 carbon atoms, in particular having 2 to 17 carbon atoms. In these radicals, in addition, at least one CH₂ group may be replaced by heteroatoms, such as oxygen, sulfur or by groups such as —NR³—, —C(O)—O—, —C(O)—NR³—,

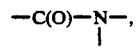

—NR³—C(O)—NR³—, —O—C(O)—NR³—,

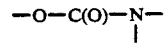

or —O—C(O)—O—, or CH groups may be replaced by

Particularly preferred aliphatic or araliphatic radicals are those variants in which a maximum of two CH₂ groups have been replaced by one type of the above-mentioned groups. If CH₂ groups are replaced by heteroatoms, the maximum number of these can preferably be 5, in particular 3. It is particularly preferred if all the CH₂ groups to be replaced are replaced by heteroatoms of one type.

An unsubstituted, saturated or unsaturated aliphatic radical X contains, in the preferred variant, a maximum of 6 carbon atoms. Unsaturated aliphatic radicals X include, in particular, those whose CH₂ or CH groups are not replaced by heteroatoms or the above-mentioned groups. In their particular embodiment, they contain a maximum of one C—C multiple bond; the number of chain members in a radical of this type is particularly preferably 4. The said radicals X are preferably trivalent.

If CH₂ groups in the aliphatic radicals X are replaced by heteroatoms, these are preferably surrounded by alkylene radicals having at least two CH₂ groups each. If sulfur is the heteroatom in the aliphatic radical X, it particularly preferably occurs only once per radical. It is, in particular, surrounded by alkyl radicals having a maximum of three CH₂ groups each. If oxygen is employed as the heteroatom in the aliphatic radical, it can occur more frequently per radical, in particular 2 to 4 times. In this case, the alkylene radicals containing two oxygen atoms contain at least three CH₂ groups.

If the number of carbon atoms in the unsubstituted aliphatic radical is greater than 3, this alkylene radical is, in particular, in the form of a branched isomer. The t-butyl and t-pentyl radicals are particularly preferred.

The radical X may also contain a plurality of alkyl radicals, in particular t-butyl or t-pentyl radicals, bonded via heteroatoms or the above-mentioned groups replacing CH₂ groups. This is particularly preferred if these radicals are more than divalent.

If the t-butyl or t-pentyl radical is trivalent, m is at least 3. Preferably m=4 is achieved by a divalent t-pentyl or t-butyl radical occurring twice in the radical X. Also, m=4 is achieved by a divalent propyl radical occurring twice in the radical X.

Preferably m=6 is achieved by two trivalent radicals (t-butyl or t-pentyl) or three divalent propyl radicals occurring in the radical X. Also, m=8 is achieved, for example, by the combination of 4 divalent radicals or 2 trivalent radicals with one divalent radical.

The valency of the radical X in excess of two can also be achieved by the presence of heteroatoms which are more than divalent: if one CH group in the aliphatic radical X is replaced by

m values of 3 can be achieved. If two CH groups are replaced by

m can achieve a maximum of 4.

In all cases in which CH groups in the radical X are replaced by

it is preferred that no substitution of a $CH_2$ group by a further heteroatom or by one of the above-described groups takes place. The number of $CH_2$ groups between the nitrogen heteroatom and the radical of the general formula I bonded to the radical X is at least 2, in particular 2.

Pure, i.e. unsubstituted, cycloaliphatic radicals are not preferred as variants of the radical X. A specific example of a cycloaliphatic radical is, in particular, the cyclohexyl radical. However, it may be substituted, in particular by hydroxyl and/or alkyl or alkylene, the valency thereof preferably being determined by the number of alkylene substituents on the cycloaliphatic radical. Very particular preference is given to a cyclohexyl radical which carries four methylene groups as substituents, which ensure the bonding of the α-diazo-β-keto ester units and sulfonate units as in the general formula I (m=5).

The cycloaliphatic radicals as variants of the radical X are usually more a combination of a cycloaliphatic moiety and a chain-like aliphatic moiety. In this case, the cycloaliphatic moiety is preferably not substituted by replacing $CH_2$ groups from this moiety with heteroatoms or groups from the above-mentioned series.

An exception is a six-membered ring (heterocyclic ring) comprising three carboxamide units in which the coupling of the α-diazo-β-keto ester units and the sulfonate units of the general formula I takes place via ethylene groups on the amido nitrogen. Therefore m is 3 and n is 1.

However, if X is a combination of a pure cycloaliphatic moiety and one or more chain-like aliphatic moieties having 2 or more carbon atoms, the cycloaliphatic moiety is, in particular, directly adjacent to a $CH_2$ group which has been replaced by one of the above-mentioned heteroatoms or groups. A particularly preferred variant is that in which the cycloaliphatic moiety is directly adjacent to a nitrogen atom, in particular the groups

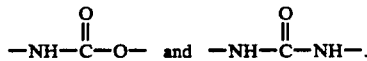

In this case, the preferred cycloaliphatic moiety is a cyclohexyl radical, which may be monovalent or divalent, the latter preferably in the 1,4-position. In both cases, the linking of one of the free valencies of the radicals

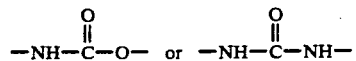

to α-diazo-β-keto ester units and sulfonate units in accordance with the general formula I takes place via an alkylene radical having at least two $CH_2$ units. If an

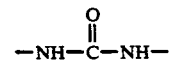

radical, the linking group is preferably a t-butylene radical. If a

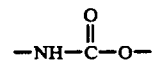

radical, i.e. the discussed linking takes place via the oxygen atom of this group, the linking group employed is preferably an ethylene radical.

If the variant of the group X is an araliphatic radical, the aromatic moiety, in particular a phenyl or, if divalent, a phenylene radical, may be bonded either via a nitrogen atom or via an oxygen atom. However, the nitrogen atom is again preferred here—if the two atoms are available for selection. An example in which the aromatic moiety is bonded directly via an oxygen atom is an ether oxygen atom bonded to the α-diazo-β-keto ester unit and/or sulfonate unit via an ethylene group. As a third variant, it is also possible in this case for the aromatic radical, in particular if it is monovalent, to be bonded via the keto group of a

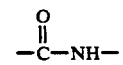

radical.

In this case, the nitrogen atom carries, in particular, an ethylene radical.

If an araliphatic radical X is present, the aliphatic moiety of the radical X which is bonded via the nitrogen atom of a radical

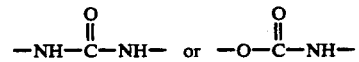

replacing a $CH_2$ group is, in particular, a t-butylene or ethylene radical; if the aliphatic moiety is bonded via the oxygen atom, it is particularly preferably an ethylene radical.

The preference for an ethylene group to be bonded via the oxygen atom of the above-mentioned groups replacing a $CH_2$ group in the radical X can also, in general, be transferred to aliphatic radicals, while both the ethylene radicals and higher aliphatic radicals, in particular comprising carbon chains having more than 3 carbon atoms, are bonded via the nitrogen atom. The t-butylene radical is preferred.

In araliphatic and aliphatic radicals X, it is preferred that a maximum of two $CH_2$ groups are replaced by radicals such as

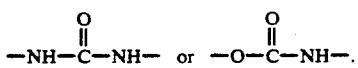

In the particular preferred embodiments, the radical

as a replacement for a CH group only occurs once in a radical X.

In the above-mentioned variants of the radicals $R^1$, $R^2$ and X, m is preferably an integer from 3 to 8 and n is an integer from 1 to 3.

Particularly preferably, m is an integer from 3 to 6, and n is particularly preferably 1 or 2.

The polyfunctional compounds of the general formula I according to the invention characterized in detail above are highly suitable as photoactive components in a radiation-sensitive mixture. In particular, the compounds according to the invention are suitable for exposure to radiation having a wavelength of from about 190 to 350 nm. The use of the novel polyfunctional compounds as photoactive components in radiation-sensitive mixtures for the preparation of high-resolution photoresists for microlithography is described in German Patent Application P 40 14 648.0, corresponding to Docket No. 16878/388, filed concurrently.

The invention also relates to a process for the preparation of the polyfunctional compounds according to the invention containing α-diazo-β-keto ester units and sulfonate units. It has proven particularly favorable first to synthesize suitable precursors for β-keto ester/sulfonates of the general formula II and to convert the latter, in a subsequent reaction, into the α-diazo-β-keto ester/sulfonates of the formula I by so-called diazo transfer (cf. M. Regitz et al., Org. Prep. Proced., 1, 99 (1969)):

ferred solvents are those which have a boiling point of from about 30° C. to 140° C. The actual reaction according to the invention can be carried out by 3 variants.

VARIANT A

The cooled solution is treated with about a 1- to 1.3-fold excess (based on the number of activated methylene groups to be reacted) of a diazo transfer reagent. Suitable transfer reagents are, in particular, aromatic and aliphatic sulfonyl azides, such as toluenesulfonyl azide, 4-carboxyphenylsulfonyl azide, 2-naphthalenesulfonyl azide or methylsulfonyl azide. The equimolar amount, based on the sulfonyl azide, of a base, preferably of a tertiary amine, is then added to the solution. The temperature of the mixture must be kept constant during this operation. Examples of preferred amines are triethylamine, triisopropylamine or diazobicyclo[2.2.2]octane. It is particularly preferred to use triethylamine as the base. The mixture obtained is stirred at the prespecified temperature for from about 5 to 50 minutes, preferably from 10 to 15 minutes, warmed to room temperature and stirred for a further 1 to 24 hours, preferably 2 to 4 hours. Depending on the type of sulfonyl azide employed, the resultant sulfonyl amide may precipitate, so that it can be filtered off, if desired, when the reaction is complete.

VARIANT B

As an alternative to variant A, it is also possible to add the sulfonyl azide to the β-keto ester/sulfonate of the general formula II and the amine initially introduced under the above-described conditions while maintaining the temperature.

VARIANT C

However, a modified variant A has proved particularly favorable in which the solution of the β-keto ester/sulfonate of the general formula II is first treated with only about a 0.7- to 0.9-fold excess (based on the number of activated methylene groups to be reacted) of

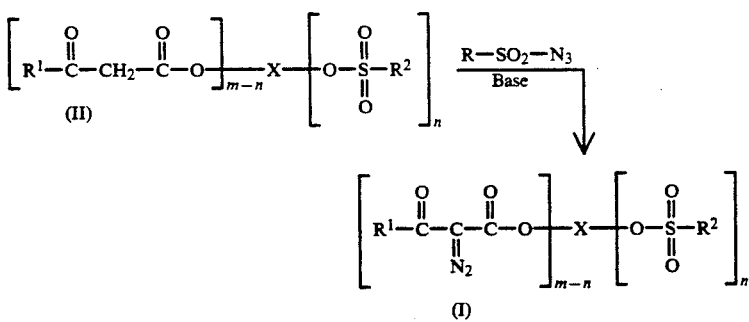

To this end, a β-keto ester/sulfonate of the general formula II (in which $R^1$, $R^2$ and X are as defined in the formula I) is dissolved in from about 5 to 50 times, preferably 10 times, the amount of a suitable solvent (based on the mixture), and the solution is cooled to a temperature from about −15° C. to +15° C., preferably from about −5° C. to +5° C. Suitable solvents are alcohols, such as methanol and ethanol, alcohol ethers, such as ethylene glycol monomethyl ether, chlorinated hydrocarbons, such as dichloromethane and trichloromethane, or preferably aliphatic nitriles, such as acetonitrile, or mixtures of these solvents. Particularly prea sulfonyl azide, preferably toluenesulfonyl azide, and all the amine is added while maintaining the prespecified temperature. The mixture is then stirred, if desired, with warming to room temperature. After from about 10 to 120 minutes, the toluenesulfonyl azide is no longer detectable by chromatography. The mixture is then recooled, if necessary, and this time treated with about a 0.6 to 0.1-fold excess of 4-carboxyphenylsulfonyl azide, giving a total excess of sulfonyl azide corresponding to variant A. The crude products prepared by this variant have high purity.

The mixture obtained by variants A to C is freed from solvent and excess reagents and taken up in an inert, water-immiscible solvent, in particular dichloromethane or diethyl ether. The mixture is washed twice with 5 to 25% strength potassium hydroxide solution to remove the sulfonyl amide residues and subsequently washed with water until neutral, dried over a suitable desiccant and again freed from solvent. The residue which remains, comprising, in particular when variant C is used, virtually exclusively pure α-diazo-β-keto ester/sulfonate of the general formula I, can be worked up by known methods, for example by crystallization or chromatography.

The β-keto ester/sulfonate of the general formula II which is necessary for conversion into the polyfunctional compounds of the general formula I according to the invention containing α-diazo-β-keto ester units and sulfonate units can be prepared in various ways known from the literature:

1. In accordance with scheme 2, a reaction takes place between a monofunctional 5-acyl-2,2-dialkyl-1,3-dioxane-4,6-dione (5-acyl derivative of Meldrum's acid) of the general formula III and a polyhydric alcohol sulfonate of the general formula IV to give the polyfunctional β-keto ester/sulfonate of the general formula II. The preparation of 5-acyl derivatives of Meldrum's acid of the general formula III and their conversion into β-keto esters is known for monofunctional compounds and can be carried out, for example, analogously to the procedures of Y. Oikawa et al., J. Org. Chem., 43, 2087 (1987), by reacting acid chlorides with Meldrum's acid, or analogously to the procedures of P. Houghton and D.J. Lapham, Synthesis, 1982, 451 ff. Examples of the conversion into polyfunctional β-keto esters in accordance with the above-mentioned literature can also be found in German Patent Applications P 39 00 735.9 and P 39 00 736.7 (corresponding to U.S. Ser. Nos. 07/464,003 and 466,007, respectively), which are not pre-priority publications. The products are isolated in their enol form.

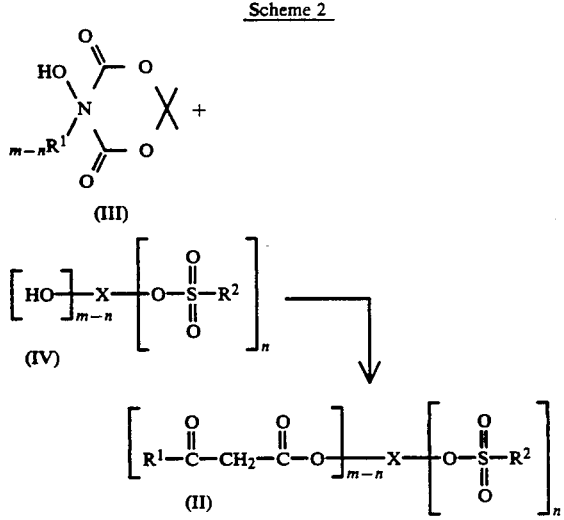

2. In accordance with scheme 3, the reaction takes place between a monofunctional β-keto ester, preferably a methyl or ethyl ester of the general formula V, with a polyhydric alcohol/sulfonate of the general formula IV to give the polyfunctional β-keto ester of the general formula II. The transesterification reaction for the preparation of monofunctional β-keto esters is known and is described by A.R. Bader et al. in J. Am. Chem. Soc., 73, 4195 ff., (1951).

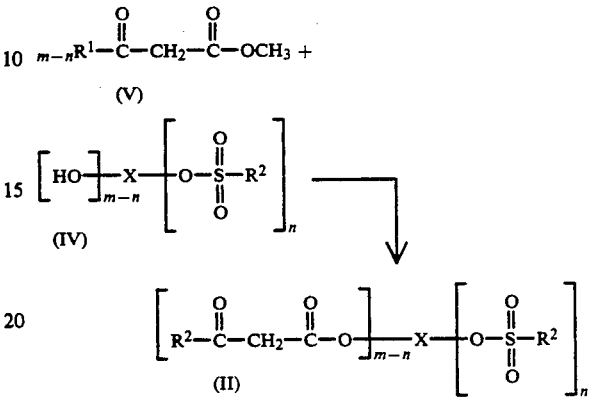

In the reaction sequence of scheme 2, the particular 5-acyl derivative of Meldrum's acid of the general formula III is treated with the amount necessary to give the desired degree of reaction of the particular polyfunctional alcohol sulfonate of the general formula IV, the mixture is subsequently dissolved in from about 5 to 20 times, preferably 10 times, the amount of a solvent which does not react with alcohols or Meldrum's acid, for example a ketone, such as acetone or ethyl methyl ketone, or an ether, such as 1,2-dimethoxyethane, or dioxane, if necessary with heating. The clear solution is heated to a temperature of from about 60° to 120° C., preferably to from 80° to 100° C. The commencement of the reaction can be seen from the vigorous evolution of carbon dioxide. The mixture is stirred at the prespecified temperature for from about 1 to 6 hours, preferably 2 to 3 hours, until $CO_2$ evolution can no longer be observed.

The solvent is subsequently removed in vacuo. Although the particular β-keto ester/sulfonate of the general formula II is produced in high purity, the product may, if desired, be further purified by methods known to those skilled in the art.

Particularly suitable 5-acyl derivatives of Meldrum's acid of the general formula III are those in which $R^1$ is cyclobutyl, butyl, pentyl, cyclopentyl, hexyl, cyclohexyl, heptyl, octyl, nonyl, adamantyl or higher alkyl radicals having up to about 22 carbon atoms, which may be substituted, if desired, by further alkyl radicals, alkoxyalkyl radicals, aryl radicals, alkoxyaryl radicals, aryloxyaryl radicals, halogen atoms or by other polyfunctional groups, for example by terminal acid ester functions, or in which individual $CH_2$ groups may be replaced by oxygen or sulfur atoms or by groups such as —C(O)—O—, —C(O)—NR$^3$—, —NR$^3$—C(O)—NR$^4$—, —O—C(O)—NR$^3$—, —O—C(O)—O— or —NR$^3$—, in which $R^3$ and $R^4$ are as defined above.

Particularly preferred radicals $R^1$ are 2-phenylethyl, t-butyl, n-hexyl, 2,5-dioxahexyl, cyclopentyl, cyclohexyl, benzyl, phenoxymethyl and nonyl. The t-butyl, cyclohexyl and phenoxymethyl radicals are especially preferred.

The alcohol sulfonates of the general formula IV which are necessary for the reaction as in scheme 2 can be prepared by various procedures known from the literature:

1) Corresponding to scheme 4, the reaction of the polyfunctional alcohols of the formula VI is carried out with appropriate reagents to form partially protected alcohols of the general formula VII. The hydroxyl group or groups which are still free are reacted with sulfonyl chlorides of the general formula VIII in the presence of a base to give the protected alcohol sulfonates of the general formula IX. Removal of all the protective groups present gives the polyfunctional alcohol sulfonates of the general formula IV. The protective group technique is described in detail by T.W. Greene in "Protective Groups in Organic Synthesis", 1st Edition, pp. 10–113, Wiley & Sons, New York, 1981, with reference to various examples.

In the reaction sequence according to scheme 4, the particular polyfunctional alcohol of the general formula VI is treated with the amount of a suitable protective-group reagent necessary for the desired degree of conversion and a catalytic amount of an acid, giving partially protected alcohols of the general formula VII. The type and amount of the protective-group reagents used depend on the structure of the polyfunctional alcohols VI. The acid and the chosen reaction conditions depend on the protective-group reagent used. Since bases are employed for deprotonation in the formation of the protected sulfonates of the general formula IX, the protected alcohols of the general formula VII must be base-stable. Products of the reaction of alcohols with protective group-forming reagents are, in particular, substituted methyl and ethyl ethers, silyl ethers, esters,

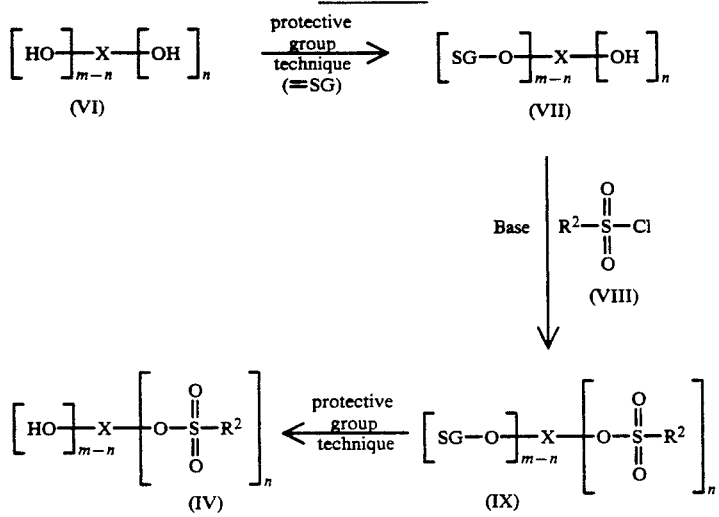

2) In accordance with scheme 5, the reaction takes place between a polyhydric alcohol of the general formula VI and the desired amount of a monofunctional sulfonyl chloride of the general formula VIII to give mono- (m=3, 4 or 5), bis- (m=6 or 8) and trifunctional (m=8) sulfonates and/or an isomeric mixture of various sulfonate-containing alcohols of the general formula IV. The preparation of sulfonates from alcohols is known for monofunctional compounds and is described in detail, for example, by E. Schaumann in "Methoden der organischen Chemie" [Methods of Organic Chemistry] (Houben-Weyl-Müller, Eds.), 4th Edition, Vol. 6/1b, p. 874, Thieme-Verlag, Stuttgart, 1984, and the literature cited therein.

carbonates, cyclic acetals and ketals and cyclic ortho-esters. For alcohols of the general formula VI which contain 1,2- or 1,3-hydroxyl groups, cyclic acetals and ketals and ortho-esters are possible. Preference is given to reagents which result in the formation of cyclic ketals, particular preference being given to acetonide-(isopropylidene-)protected 1,2- and 1,3-alcohols.

Acetonides (1,2- or 1,3-O,O-isopropylidene ketals) can be obtained by reacting 1,2- and 1,3-alcohols of the general formula VI with, for example, 2-methoxypropene, 2-ethoxypropene, 2-(trimethylsilyloxy)propene, acetone or 2,2-dimethoxypropane in the presence of catalytic amounts of acid. Particular preference is given to the reaction of alcohols containing 1,2- or 1,3-hydroxyl groups in anhydrous acetone, since the protective group-forming reagent simultaneously functions as the solvent here.

In the reaction sequence of scheme 4, the alcohols containing 1,2- or 1,3-hydroxyl groups are warmed with about 2 to 20 times, preferably 5 to 12 times, the amount of acetone. If necessary, one or more further solvents may be added in order to achieve better solubility or to correspondingly increase the reaction temperature. After addition of a catalytic amount of acid, preferably p-toluenesulfonic acid, the mixture is stirred for from about 1 to 24 hours, preferably from 3 to 8 hours at about 20° to 85° C., preferably at 35°-60° C., and subsequently treated with about 1 to 10 times, preferably 2 to 5 times, the amount of potassium carbonate

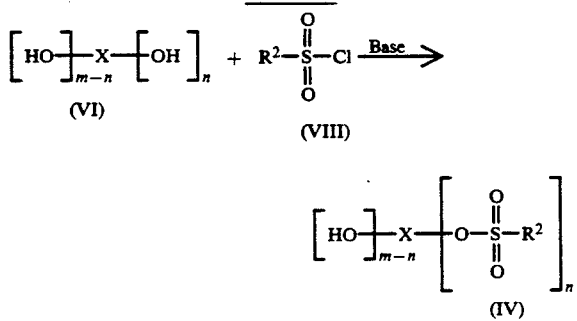

(based on the amount of p-toluenesulfonic acid employed) or another base.

After cooling, the mixtures, which are usually cloudy, are filtered via a separation aid, such as Hydro Super Gel, kieselguhr, silica gel, etc. The solvent is subsequently removed by vacuum distillation. The product is purified by methods known to a person skilled in the art, for example by high-vacuum distillation.

Polyfunctional alcohols of the general formula VI which contain no 1,2- or 1,3-hydroxyl groups are protected, in particular, by conversion into ethers. Substituted methyl ethers and silyl ethers are preferred. Tetrahydropyranyl ethers are particularly preferred. These are preferably synthesized by two different routes, described by A. Bongini, G. Cardillo, M. Orena, S. Sandri, Synthesis 1979, 618 (Variant A) and by M. Miyashita, A. Yoshikoshi, P.A. Grieco, J. Org. Chem. 42 (1977) 3772 (Variant B).

VARIANT A

In the reaction sequence of scheme 4, the alcohols containing no 1,2- or 1,3-hydroxyl groups are dissolved with an amount corresponding to the desired degree of reaction of 3,4-dihydro-2H-pyran in about 1 to 20 times, preferably 2 to 10 times, the amount of hexane, and added to a suspension of acidic ion exchanger resin (Amberlyst H-15, 0.05 to 2 times, preferably 0.1 to 0.5 times the amount, based on the amount of hydroxyl groups employed) in hexane (amount as above). If necessary, one or more further solvents, such as, for example, methanol, can be added in order to achieve better solubility. The mixture is stirred at from about 0° to 85° C., preferably at from 20° to 50° C., for from about 0.5 to 24 hours, preferably from 1 to 5 hours, and the resin is subsequently filtered off. The solvent is subsequently removed by vacuum distillation. The residue which remains, which contains virtually exclusively the isomeric alcohols, is separated by chromatography.

VARIANT B

In the reaction sequence of scheme 4, the alcohols containing no 1,2- or 1,3-hydroxyl groups are dissolved with an amount corresponding to the desired degree of reaction of 3,4-dihydro-2H-pyran in about 5 to 300 times, preferably 20 to 100 times, the amount of dichloromethane, and treated with pyridinium p-toluenesulfonate (from 0.02 to 1 times, preferably from 0.05 to 0.3 times, the molar amount, based on the number of hydroxyl groups to be reacted). If desired, further solvents may be added. The mixture is subsequently stirred at from about 0° to 80° C., preferably at from 10° to 45° C., for from about 0.5 to 48 hours, preferably 2.5 to 8 hours, and subsequently treated with about 5 to 100 times, preferably 10 to 50 times, the amount of ether (based on the amount of solvent employed). The product is washed with partially saturated solutions of sodium chloride and with water. The mixture is dried using sodium sulfate, and the solvent is removed by vacuum distillation. The residue which remains, which contains virtually exclusively the isomeric alcohols, is separated by chromatography.

The partially protected alcohol of the general formula VII, corresponding to the desired degree of reaction, is obtained as the main product in both variants.

The hydroxyl group or groups which are still free in the partially protected alcohols of the general formula VII are reacted with sulfonyl chlorides of the general formula VIII in the presence of a base, giving the protected alcohol sulfonates of the general formula IX.

In the reaction sequence of scheme 4, the partially protected alcohols of the general formula VII are dissolved with about 0.5 to 40 times, preferably 2 to 10 times, the amount of a base and stirred at from about −40° to 65° C., preferably at from −15° to 25° C., for from about 0.1 to 10 hours, preferably 0.5 to 1 hour. Particularly preferred bases are basic amines, such as, for example, pyridine, triethylamine, N-methylmorpholine, etc., but N-methylmorpholine is very particularly preferred. If desired, one or more further solvents, such as, for example, acetonitrile, may be added in order, for example, to achieve better solubility or to increase the reaction rate. The desired sulfonyl chloride VIII (about 1 to 3 times, preferably 1.05 to 1.5 times, the amount, based on the hydroxyl groups still present in the alcohol employed) is then added to the mixture, which is stirred at from about −40° to 65° C., preferably at from −15° to 25° C., for from about 0.5 to 48 hours, preferably 2 to 8 hours. Dichloromethane/water is subsequently added to the mixture, the organic phase is washed until neutral by methods known to a person skilled in the art and dried using sodium sulfate, and the solvent is removed by vacuum distillation.

Although the residues which remain principally comprise the partially protected alcohol sulfonates of the general formula IX (and are generally employed in the next step without further purification) the product can, if desired, be further purified by methods known to a person skilled in the art.

In the reaction sequence of scheme 4, the protective groups of the partially protected alcohol sulfonates of the general formula IX are all removed in the presence of a catalytic amount of acid, giving the alcohol sulfonates of the general formula IV. The type and amount of acid used depends on the protective group employed above. Thus, acetonide protective groups (O,O-isopropylidene acetals) are preferably removed using aqueous HCl solutions of various concentration, using acetic acid, using p-toluenesulfonic acid and/or using acidic ion exchanger resins. The same reagents are used to cleave the tetrahydropyranyl ethers into the corresponding alcohols.

In the cleavage of the cyclic ethers as in scheme 4, the partially protected alcohol sulfonates of the general formula IX are dissolved in from about 5 to 200 times, preferably 10 to 50 times, the amount of a solvent, and treated with aqueous hydrochloric acid until the pH is $\approx 1$. The solvents used are alcohols, ethers, water, organic acids, ketones or mixtures of these solvents. Preference is given to alcohols and ethers, such as, for example, methanol or tetrahydrofuran, but also mixtures comprising tetrahydrofuran, acetic acid or dilute hydrochloric acid and water. Methanol is particularly preferred. A catalytic amount of p-toluenesulfonic acid is subsequently added, and the mixture is stirred at from about −25° to 80° C., preferably at from 0° to 45° C., for from about 1 to 18 hours, preferably 2 to 7 hours. The pH of the mixture is subsequently adjusted to slightly alkaline (pH $\approx 8$ to 9) by adding alcoholic potassium hydroxide solution, and the solvent is removed by vacuum distillation. The residue is separated by column chromatography on silica gel, giving the desired alcohol sulfonates of the general formula IV, usually as colorless compounds. Preferred eluents for the column chromatography are dichloromethane, ethyl acetate, ether, hexane, petroleum ethers of various boiling fractions, tetrahydrofuran, trichloromethane and mixtures of these eluents. Dichloromethane and mixtures thereof are particularly preferred.

In accordance with scheme 5, the reaction between a polyhydric alcohol of the general formula VI containing no 1,2- or 1,3-hydroxyl groups and sulfonyl chlorides can also be carried out without using protective-group techniques. The reaction with the desired amount of a monofunctional sulfonyl chloride of the general formula VIII gives mono (m=3, 4 or 5), bis- (m=6 or 8) and trifunctional (m=8) sulfonates and/or an isomer mixture of various sulfonate-containing alcohols of the general formula IV.

The same conditions as described explicitly for the reaction step VII-IX in scheme 4 apply to these reactions.

The alcohols of the general formula VI may be trifunctional, tetrafunctional or higher-functional alcohols; preference is given to alcohols which contain from 3 to 6 OH groups per molecule.

Trifunctional alcohols are preferably derived from glycerol, from higher $\alpha,\beta,\omega$-triols or from triethanolamine, it also being possible to use longer-chain derivatives, in particular ethoxylated compounds, such as, for example, 1,3,5-tris(2-hydroxyethyl)cyanuric acid, equally well here. Specific mention is made of glycerol, 2-hydroxymethyl-2-methylpropane-1,3-diol, 2-ethyl-2-hydroxymethylpropane-1,3-diol, 2,3-isopropylideneerythruronic acid, hexane-1,2,6-triol, 1,1,1-triethanolamine, 1,1,1-tripropanolamine and partially acetalated or ketalated sugar derivatives.

In addition, products of the reaction of tetrafunctional alcohols or aminotriols with acid derivatives, isocyanates or cyclic carbonates can also be used. Higher-functional alcohols of the general formula VI are derived, for example, from products of the condensation of glycerol, or of pentaerythritol or from products of the reaction of bifunctional acid derivatives or isocyanates with higher-functional alcohols or amino alcohols. The list of alcohols which can be used is thus not complete by far; virtually any alcohol can be used which contains no group which is reactive toward acid esters, or which reacts under the reaction conditions described clearly to form esters.

In the preparation of $\beta$-keto ester/sulfonates of the general formula II by transesterification as in scheme 3, monofunctional $\beta$-keto esters of the general formula V are employed with alcohol sulfonates of the general formula IV by reacting about a 5 to 200%, preferably a 10 to 50%, excess of a $\beta$-keto ester, for example a methyl or ethyl ester, which has been esterified with a low-molecular-weight alcohol, at from about 100° to 160° C., preferably at from 120° to 140° C. In order to increase the solubility of the alcohol sulfonate of the general formula IV in the $\beta$-keto ester of the formula V, a solubilizer, such as dimethyl-formamide or N-methylpyrrolidone, may be added if necessary. The equilibrium can be shifted continuously in the desired direction by applying a weak vacuum of from about 800 to 20 mm Hg, preferably from 400 to 100 mm Hg, due to the lower alcohol formed distilling off. After the theoretical amount of lower alcohol has distilled off, the excess $\beta$-keto ester of the general formula V, which has a low degree of esterification, and, if appropriate, the solubilizer added are removed by distillation in a high vacuum. The residue remaining is the $\beta$-keto ester/sulfonate of the general formula II, which is frequently produced in oily form and usually in very high purity, so that it can be used for the diazo transfer without further purification.

Some of the $\beta$-keto esters of the general formula V with a low degree of esterification which are necessary in this reaction sequence are commercially available and some can be prepared by numerous methods known from the literature. Particular preference is given here to their preparation from the corresponding 5-acyl derivatives of Meldrum's acid of the general formula III. Although an additional reaction step is carried out here compared with process variant 1, better yields and/or higher purity $\beta$-keto ester/sulfonates of the general formula II can be achieved using this variant.

Said compounds according to the invention are used in radiation-sensitive mixtures. They have high photosensitivity, in particular on irradiation with light having a wavelength of between 190 and 300 nm. Since the mixtures bleach out very well on exposure, structuring can be achieved which is clearly superior to that of the known mixtures with respect to resolution capacity. The use of the radiation-sensitive compounds according to the invention is described in German Patent Application P 40 14 648.0 (corresponding to U.S. Ser. No. 07/694,353, filed concurrently).

The examples below for the preparation of the novel polyfunctional compounds of the general formula I containing $\alpha$-diazo-$\beta$-keto ester units and sulfonate units describe the invention, without representing a limitation.

EXAMPLE 1

Preparation of a trifunctional ester of the general formula I containing two $\alpha$-diazo-$\beta$-keto ester units and one sulfonate unit: the 4-tert-butylphenylsulfonate of 2,10-diazo-1,11-dicyclohexyl-4,8-dioxa-6-ethyl-6-(hydroxymethyl)-1,3,9,11-tetraoxoundecane (5)

Step 1:
2,2-dimethyl-5-ethyl-5-(hydroxymethyl)-1,3-dioxane (1)

2.75 g of p-toluenesulfonic acid are added to 275 g (2.05 mol) of 2,2-bis(hydroxymethyl)-1-butanol in 1.4 l of acetone, and the mixture is heated to reflux. After 4 hours, the solution is neutralized while still hot by adding 8.25 g of potassium carbonate, and the mixture is stirred for a further 30 minutes and subsequently allowed to stand overnight at room temperature. The turbid mixture is filtered through kieselguhr, and the solvent is removed by distillation in vacuo, leaving 400 ml of a turbid, oily residue, which is purified by distillation in a high vacuum, giving 224 g of the alcohol 1 as a colorless oil.

Step 2:
4-tert-butylphenylsulfonate of 2,2-dimethyl-5-ethyl-5-(hydroxymethyl)-1,3-dioxane (2)

6.97 g (40 mmol) of the above-described compound 1 are introduced, with 8.6 g (85 mmol) of N-methylmorpholine, into 50 ml of acetonitrile, and the mixture is cooled to 0° C. and stirred. After 30 minutes, 10.0 g (43 mmol) of 4-tert-butylphenylsulfonyl chloride are added to the solution. The mixture is stirred for 7 hours at 0° C., and left to stand overnight at −20° C. The mixture is warmed to room temperature, and the solvent is removed by distillation in vacuo. 150 ml of water and 100 ml of dichloromethane are added to the oily residue which remains. The organic phase is separated off, and the aqueous phase is then extracted with dichloromethane. The combined organic phases are washed three times with 100 ml of semisaturated potassium dihydrogen phosphate solution in each case and twice with 150 ml of water in each case, and dried over sodium sulfate, and the solvent is removed by distillation in vacuo, leaving 12 g of a yellow oil, which comprises virtually exclusively the protected sulfonate 2. The latter is used without further purification as a starting material for the next step.

Step 3:

4-tert-butylphenylsulfonate of 2,2-bis(hydroxymethyl)-1-butanol (3)

11.1 g (30 mmol) of the sulfonate 2 prepared in step 2 are introduced into 100 ml of methanol, and 3 N hydrochloric acid is added dropwise until the pH is less than 5. 250 mg of p-toluenesulfonic acid are subsequently added, the mixture is stirred at room temperature for 4.5 hours, and methanolic potassium hydroxide solution is added until the mixture is slightly alkaline (pH $\approx$ 8 to 9). The solvent is removed by distillation in vacuo, leaving a yellow-orange, oily residue, which is separated by column chromatography on silica gel using dichloromethane as eluent, giving 6.4 g of a colorless oil 3, which partially crystallizes.

Step 4:

4-tert-butylphenylsulfonate of 1,11-dicyclohexyl-4,8-dioxa-6-ethyl-6-(hydroxymethyl)1,3,9,11-tetraoxoundecane (4)

3.2 g (9.7 mmol) of the above-described compound 3 are introduced, with 4.9 g (19.4 mmol) of 5-(1-cyclohexyl-1-hydroxymethylidene)-2,2-dimethyl-1,3-dioxane-4,6-dione, into 20 ml of acetone, and the mixture is slowly warmed. Vigorous evolution of carbon dioxide commences from about 60° C. The solution is refluxed for 2.5 hours, and the solvent is removed by distillation in vacuo. The reaction mixture is cooled, leaving a dark red oil, which contains the desired $\beta$-keto ester/sulfonate 4 and is used without further purification as a starting material for the next step.

Step 5:

4-tert-butylphenylsulfonate of 2,10-diazo-1,11-dicyclohexyl-4,8-dioxa-6- ethyl- 6-(hydroxymethyl)-1,3,9,11-tetraoxoundecane (5)

The above-described compound 4, in the amount produced, is dissolved in 50 ml of acetonitrile, and the solution is cooled to 0° C. 2.37 g (12 mmol) of tosyl azide are added to the cooled solution with stirring, and 2.5 g (25 mmol) of triethylamine are subsequently added dropwise at such a rate that the temperature does not exceed 5° C. The mixture is stirred at this temperature for 2 hours, and is subsequently warmed to room temperature. After 2 hours, tosyl azide is no longer detectable in the mixture by thin-layer chromatography (silica gel, dichloromethane as eluent). 1.70 g (7.5 mmol) of 4-carboxyphenylsulfonyl azide are added to the mixture at 0° C., and the mixture is stirred for 15 minutes. After a further 2 hours at room temperature, the solvent is removed by distillation in vacuo. The residue is taken up in 100 ml of dichloromethane, and the solution is washed four times with 50 ml of a 25% strength aqueous potassium hydroxide solution in each case. The solution is subsequently washed with water until neutral, and the organic phase is dried over sodium sulfate. Evaporation leaves an orange-red oil, which is substantially freed from solvent residues by applying a high vacuum. Column chromatography on silica gel using dichloromethane/hexane (1:1) as eluent gives 1.8 g of virtually colorless product 5, which has the following composition.

$C_{34}H_{46}N_4O_9S$ calc.: C 59.5% H 6.8% N 8.2% S 4.7%
(MW 686.8) found: C 59.9% H 6.8% N 8.0% S 4.4%
IR (KBr): 2,136 cm$^{-1}$ (C=N$_2$)

EXAMPLE 2

Preparation of a trifunctional ester of the general formula I containing two $\alpha$-diazo-$\beta$-keto ester units and one sulfonate unit: the 2-(benzoylaminomethyl)thiophene-5-sulfonate of 2,10-diazo-1,11-dicyclohexyl-4,8-dioxa-6-ethyl-6-(hydroxymethyl)-1,3,9,11-tetraoxoundecane (9)

Step 1:

2,2-Dimethyl-5-ethyl-5-(hydroxymethyl)-1,3-dioxane (1) Preparation see Example 1, step 1

Step 2:

2-(Benzoylaminomethyl)thiophene-5-sulfonate of 2,2-dimethyl-5-ethyl-5-(hydroxymethyl)-1,3-dioxane (6)

3.26 g (18.7 mmol) of the partially protected alcohol 1 and 8.09 g (80 mmol) of N-methylmorpholine are cooled to 0° C. and stirred. After 10 minutes, 6.5 g (21 mmol) of 2-(benzoylaminomethyl)thiophene-5-sulfonyl chloride are added in portions. The mixture is stirred at 0° C. for 3 hours and at room temperature for 30 minutes, and 30 ml of dichloromethane and 150 ml of ice water are added. The organic phase is separated off, and the aqueous phase extracted three times with 50 ml of dichloromethane in each case. The combined organic phases are washed until neutral, and dried using sodium sulfate, and the solvent is removed by distillation in vacuo. The final solvent residues are removed virtually completely in a high vacuum, leaving 7.5 g of a dark red, viscous oil, which contains the sulfonate 6 and is used without further purification as a starting material for the next step.

Step 3:

2-(benzoylaminomethyl)thiophene-5-sulfonate of 2,2-bis(hydroxymethyl)-1-butanol (7)

7.8 g (17 mmol) of the crude sulfonate 6 prepared in step 2 are introduced into 60 ml of methanol, and 3 N hydrochloric acid is added dropwise until the pH is less than 5. 400 mg of p-toluenesulfonic acid are subsequently added, the mixture is stirred at room temperature for 21 hours, and methanolic potassium hydroxide solution is added until the mixture is slightly alkaline (pH $\approx$ 8 to 9). The solvent is removed by distillation in vacuo, and the residue which remains is separated by column chromatography on silica gel using dichloromethane as the eluent, giving 4.1 g of a colorless oil 7.

Step 4:

2-(benzoylaminomethyl)thiophene-5-sulfonate of 1,11-dicyclohexyl-4,8-dioxa-6-ethyl-6-(hydroxymethyl)-1,3,9,11-tetraoxoundecane (8)

4.1 g (9.9 mmol) of the above-described compound 7 are introduced, with 5.3 g (20.8 mmol) of 5-(1-cyclohexyl-1-hydroxymethylidene)-2,2-dimethyl-1,3-dioxane-4,6-dione, into 20 ml of acetone, and the mixture is slowly warmed. Vigorous evolution of carbon dioxide commences from about 60° C. The solution is refluxed for 2 hours, and the solvent is subsequently removed by distillation in vacuo. After cooling, an oily, black-brown residue remains, which contains (in addition to other compounds) the desired $\beta$-keto ester/sulfonate 8 as the main product. It is used without purification as a starting material for the next step.

Step 5:

2-(benzoylaminomethyl)thiophene-5-sulfonate of 2,10-diazo-1,11-dicyclohexyl-4,8-dioxa-6-ethyl-6-(hydroxymethyl)-1,3,9,11-tetraoxoundecane (9)

The above-described compound 8, in the amount produced in step 4, is dissolved in 35 ml of acetonitrile, and the solution is cooled to 0° C. 2.76 g (14 mmol) of tosyl azide are added to the cooled solution with stirring, and 2.02 g (20 mmol) of triethylamine are subsequently added dropwise at such a rate that the temperature does not exceed 5° C. The mixture is stirred at this temperature for 1 hour, and subsequently warmed to room temperature. After 2 hours, tosyl azide is no longer detectable in the mixture by thin-layer chromatography (silica gel, dichloromethane as eluent). 1.36 g (6.0 mmol) of 4-carboxyphenylsulfonyl azide are added to the mixture at 0° C., and the mixture is stirred for 30 minutes. After hour at room temperature, the mixture is placed in the freezer at −20° C. overnight. After the mixture has warmed to room temperature, the solvent is removed by distillation in vacuo, the residue is taken up in 120 ml of dichloromethane, and the solution is washed four times with 40 ml of 20% strength aqueous potassium hydroxide solution in each case. The solution is subsequently washed with water until neutral, and the organic phase is dried using sodium sulfate. Evaporation leaves a dark red oil, which is substantially freed from solvent residues by applying a high vacuum. Column chromatography on silica gel using dichloromethane as eluent gives 1.6 g of the α-diazo-β-keto ester/sulfonate 9, which has the following composition.

$C_{36}H_{43}N_5O_{10}S_2$ calc.: C 56.2% H 5.6% N 9.1% S 8.3%

(MW 769.9) found: C 55.7% H 5.8% N 8.3% S 8.2%
IR (KBr): 2,137 cm$^{-1}$ (C=N$_{12}$)

EXAMPLE 3

Preparation of a trifunctional ester of the general formula I containing two α-diazo-β-keto ester units and one sulfonate unit: the 4-bromophenylsulfonate of 4,12-diazo-6,10-dioxa-1,15-diphenyl-8-ethyl-8-(hydroxymethyl)-3,5,11,13tetraoxopentadecane (13)

Step 1:
2,2-dimethyl-5-ethyl-5-(hydroxymethyl)-1,3-dioxane (1) Preparation see Example 1, step 1

Step 2:
4-bromophenylsulfonate of 2,2-dimethyl-5-ethyl-5-(hydroxymethyl)-1,3-dioxane (10)

31.4 g (0.18 mol) of the partially protected alcohol 1 are introduced into 81 g (0.80 mol) of N-methylmorpholine and the mixture is cooled to 0° C. and stirred. After 30 minutes, 51 g (0.20 mol) of 4-bromophenylsulfonyl chloride are added to the solution. The mixture is stirred at 0° C. for 4 hours, and the mixture is kept at −20° C. overnight. The mixture is warmed to room temperature, and 1.0 l of ice water and 500 ml of dichloromethane are added. The organic phase is separated off, and the aqueous phase is then extracted with dichloromethane. The combined organic phases are washed four times with 250 ml of water in each case, and dried using sodium sulfate, and the solvent is removed by distillation in vacuo, leaving 74 g of a yellow oil 10, which crystallizes overnight. The protected sulfonate 10 is used without further purification as a starting material for the next step.

Step 3:
4-bromophenylsulfonate of 2,2-bis(hydroxymethyl)-1-butanol (11)

39.5 g (0.10 mol) of the protected sulfonate 10 prepared in step 2 are completely dissolved in 600 ml of methanol, and 3 N hydrochloric acid is added dropwise until the pH is less than 5. 4.0 g of p-toluenesulfonic acid are subsequently added, the mixture is stirred at room temperature overnight, and methanolic potassium hydroxide solution is added to the mixture until it is slightly alkaline (pH ≈ 8 to 9). The solvent is removed by distillation in vacuo, and the residue which remains is separated by column chromatography on silica gel using dichloromethane as eluent, giving 10.2 g of crystalline sulfonate 11.

Step 4:
4-bromophenylsulfonate of 6,10-dioxa-1,15-diphenyl-8-ethyl-8-(hydroxymethyl)-3,5,11,13-tetraoxopentadecane (12)

10.0 g (28.3 mmol) of the above-described compound 11 are introduced, with 15.6 g (56.5 mmol) of 5-(3-phenyl-1-hydroxypropylidene)-2,2-dimethyl-1,3-dioxane-4,6-dione, into 100 ml of acetone, and the mixture is slowly warmed. Vigorous evolution of carbon dioxide commences from about 60° C. The solution is refluxed for 2 hours, and the solvent is subsequently removed by distillation in vacuo. The reaction mixture is cooled, leaving a viscous, dark red oil, which contains the desired β-keto ester/sulfonate 12 as the main product. The β-keto ester/sulfonate 12 is used without further purification as a starting material for the next step.

Step 5:
4-bromophenylsulfonate of 4,12-diazo-6,10-dioxa-1,15-diphenyl-8-ethyl-8-(hydroxymethyl)-3,5,11,13-tetraoxo-pentadecane (13)

The above-described compound 12, in the amount produced in step 4, is dissolved in 250 ml of acetonitrile, and the solution is cooled to 0° C. 9.38 g (47.6 mmol) of tosyl azide are added to the cooled solution with stirring, and 6.76 g (67 mmol) of triethylamine are subsequently added dropwise at such a rate that the temperature does not exceed 5° C. The mixture is stirred at this temperature for 1 hour, subsequently warmed to room temperature and stirred at this temperature for a further 2 hours. 4.33 g (19 mmol) of 4-carboxyphenylsulfonyl azide are added to the mixture at 0° C., and the mixture is stirred for 15 minutes. After a further 2 hours at room temperature, the solvent is removed by distillation in vacuo. The residue is taken up in ether, and the solution is washed three times with 200 ml of aqueous potassium hydroxide solution (a total of 12 g of potassium hydroxide in 600 ml of water) in each case. The mixture is subsequently washed with water until neutral, and the organic phase is dried using sodium sulfate. Evaporation leaves a viscous oil, which is substantially freed from solvent residues by applying a high vacuum. Column chromatography on silica gel using dichloromethane as eluent gives the pale yellowish α-diazo-β-keto ester/sulfonate 13, which has the following composition.

$C_{34}H_{34}BrN_4O_9S$ calc.: C 54.2% H 4.4% N 7.4% S 4.3%

(MW 753.6) found: C 54.6% H 4.2% N 7.1% S 4.4%
IR (KBr): 2,140 cm$^{-1}$ (C=N$_2$)

EXAMPLE 4

Preparation of a trifunctional ester of the general formula I containing two α-diazo-β-keto ester units and one sulfonate unit: the 3-chloropropylsulfonate of 1,13-bis(phenoxy)-3,11-diazo-5,9-dioxa-7-ethyl-7-(hydroxymethyl)-2,4,10,12-tetraoxotridecane (17)

Step 1:
2,2-dimethyl-5-ethyl-5-(hydroxymethyl)-1,3-dioxane (1) Preparation see Example 1, step 1

Step 2:

3-chloropropylsulfonate of 2,2-dimethyl-5-ether-5-(hydroxymethyl)-1,3-dioxane (14)

8.71 g (50 mmol) of the partially protected alcohol 1 are introduced into 11.1 g (0.11 mol) of N-methylmorpholine, and the mixture is cooled to 0° C. and stirred. After 30 minutes, 9.74 g (55 mmol) of 3-chloropropylsulfonyl chloride are added to the solution. The mixture is stirred at 0° C. for 8 hours, and kept at −20° C. overnight. The mixture is warmed to room temperature, and the solvent is removed by distillation in vacuo. 250 ml of water and 200 ml of dichloromethane are added to the oily residue which remains. The organic phase is separated off, and the aqueous phase is then extracted with dichloromethane. The combined organic phases are washed three times with 100 ml of semisaturated potassium dihydrogen phosphate solution in each case, and twice with 150 ml of water in each case, and dried using sodium sulfate, and the solvent is removed by distillation in vacuo, leaving 13 g of a yellow oil, which contains the desired sulfonate 14 and is used without further purification as a starting material for the next step.

Step 3:

3-chloropropylsulfonate of 2,2-bis(hydroxymethyl)-1-butanol (15)

11.1 g (40 mmol) of the protected sulfonate 14 prepared in step 2 are introduced into 150 ml of methanol/50 ml of tetrahydrofuran, and 3 N hydrochloric acid is added dropwise until the pH is less than 5. 0.50 g of p-toluenesulfonic acid is subsequently added, the mixture is stirred at room temperature for 3.5 hours, and methanolic potassium hydroxide solution is added until the mixture is slightly alkaline (pH≈8 to 9). The solvent is removed by distillation in vacuo, leaving a yellow-orange, oily residue, which is separated by column chromatography on silica gel using dichloromethane as eluent, giving 7.2 g of a colorless oil 15.

Step 4:

3-chloropropylsulfonate of 1,13-bis(phenoxy)-5,9-dioxa-7-ethyl-7-(hydroxymethyl)-2,4,10,12-tetraoxotridecane (16)

3.2 g (11.6 mmol) of the above-described compound 15 are introduced, with 6.46 g (23.2 mmol) of 5-(2-phenoxy-1-hydroxyethylidene)-2,2-dimethyl-1,3-dioxane-4,6-dione, into 25 ml of acetone, and the mixture is slowly warmed. Vigorous evolution of carbon dioxide commences from about 60° C. The solution is refluxed for 2 hours, and the solvent is subsequently removed by distillation in vacuo. The reaction mixture is cooled, leaving a red-black oil, which contains (in addition to other products) the desired β-keto ester/sulfonate 16, which is used without further purification as a starting material for the next step.

Step 5:

3-chloropropylsulfonate of 1,13-bis(phenoxy)-3,11-diazo-5,9-dioxa-7-ethyl-7-(hydroxymethyl)2,4,10,12-tetraoxotridecane (17)

The above-described compound 16, in the amount produced, is dissolved in 50 ml of acetonitrile, and the solution is cooled to 0° C. 2.76 g (14 mmol) of tosyl azide are added to the cooled solution with stirring, and 3.1 g (30 mmol) of triethylamine are subsequently added dropwise at such a rate that the temperature does not exceed 5° C. The mixture is stirred at this temperature for 30 minutes and subsequently at room temperature for 2 hours. 2.16 g (9.5 mmol) of 4-carboxyphenylsulfonyl azide are added to the mixture at 0° C., and the mixture is stirred for 15 minutes. After 1 hour at room temperature, the solvent is removed by distillation in vacuo, the residue is taken up in dichloromethane, and the solution is washed three times with 100 ml of 20% strength aqueous potassium hydroxide solution in each case. The mixture is subsequently washed with water until neutral, and the organic phase is dried using sodium sulfate. Evaporation leaves an orange-red oil, which is substantially freed from solvent residues by applying a high vacuum. Column chromatography on silica gel using dichloromethane/hexane (1:1) as eluent gives the virtually colorless product 17, which has the following composition.

$C_{30}H_{31}ClN_4O_{11}S$ calc.: C 52.1% H 4.5% N 8.1% S 4.6%

(MW 691.1) found: C 51.9% H 4.7% N 8.0% S 4.4%

IR (Film): 2,144 cm$^{-1}$ (C=N$_2$)

EXAMPLE 5

Preparation of an isomeric mixture of two trifunctional glycerol esters of the general formula I, each of which contains two α-diazo-β-keto ester units and one sulfonate unit: the 4-(trifluoromethyl)phenylsulfonate of 3,10-diazo-5,8-dioxa-1,12-diphenyl-6-(hydroxymethyl)-2,4,9,11-tetraoxododecane and of 3,11-diazo-5,9-dioxa-1,13-diphenyl-7-hydroxy-2,4,10,12-tetraoxotridecane (22).

Step 1:

isomeric mixture of 2,2-dimethyl-4-(hydroxymethyl)-1,3-dioxolane and 2,2-dimethyl-5-hydroxy-1,3-dioxane (18)

0.25 g of p-toluenesulfonic acid is added to 9.21 g (0.10 mol) of glycerol in 80 ml of acetone, and the mixture is heated to reflux. After 4.5 hours, the solution is neutralized while still hot by adding 0.75 g of potassium carbonate, and the mixture is stirred for a further 30 minutes and subsequently allowed to stand at room temperature overnight. The turbid mixture is filtered through kieselguhr, and the solvent is removed by distillation in vacuo, leaving about 30 ml of a turbid, oily residue, which is purified by distillation in a high vacuum, giving 7.4 g of a mixture of the isomeric alcohols 18 as a colorless oil.

Step 2:

4-(trifluoromethyl)phenylsulfonate of 2,2-dimethyl-4-(hydroxymethyl)-1,3-dioxolane and of 2,2-dimethyl-5-hydroxy-1,3-dioxane (19)

6.00 g (45.4 mmol) of the above-described isomeric mixture 18 are introduced into 20.2 g (0.20 mol) of N-methylmorpholine, and the mixture is cooled to 0° C. and stirred. After 15 minutes, 12.2 g (50 mmol) of 4-(trifluoromethyl)phenylsulfonyl chloride are added to the solution. The mixture is stirred at 0° C. for 3 hours, and 150 ml of ice water and 100 ml of dichloromethane are added. The organic phase is separated off, and the aqueous phase is then extracted with dichloromethane. The combined organic phases are washed five times with 100 ml of water in each case and dried using sodium sulfate, and the solvent is removed by distillation in vacuo, leaving 13.6 g of a beige oil, which partially crystallizes. The crude product, which contains the desired sulfonate 19, is used without further purification as a starting material for step 3.

Step 3:

isomeric 4-(trifluoromethyl)phenylsulfonate of glycerol (20)

8.0 g (23.5 mmol) of the isomeric sulfonates 19 prepared in step 2 are introduced into 100 ml of methanol, and 3 N hydrochloric acid is added dropwise until the pH is less than 5. 0.50 g of p-toluenesulfonic acid is subsequently added, the mixture is stirred at room temperature for 3 hours, and methanolic potassium hydroxide solution is added until the mixture is slightly alkaline (pH≈8 to 9). The solvent is removed by distillation in vacuo, leaving a yellow-orange, oily residue. Column chromatography on silica gel using dichloromethane as eluent gives 3.1 g of a colorless oil 20.

Step 4:

4-(trifluoromethyl)phenylsulfonate of 5,8-dioxa-1,12-diphenyl-6-(hydroxymethyl)-2,4,9,11-tetraoxododecane and 5,9-dioxa-1,13-diphenyl-7-hydroxy-2,4,10,12-tetraoxotridecane (21)

2.1 g (7.0 mmol) of the isomeric glycerol sulfonates 20 are introduced, with 3.7 g (14 mmol) of 5-(1-hydroxy-2-phenylethylidene)-2,2-dimethyl-1,3-dioxane-4,6-dione, into 20 ml of acetone, and the mixture is slowly warmed. Vigorous evolution of carbon dioxide commences from about 60° C. The solution is refluxed for 2.5 hours, and the solvent is subsequently removed by distillation in vacuo. The reaction mixture is cooled, leaving a black-brown oil, which comprises virtually exclusively the desired β-keto ester/sulfonates 21. This isomeric mixture is used without further purification as a starting material for the next step.

Step 5:

4-(trifluoromethyl)phenylsulfonate of 3,10,-diazo-5,8-dioxa-1,12-diphenyl-6-(hydroxymethyl)-2,4,9,11-tetraoxododecane and of 3,11-diazo-5,9-dioxa-1,13-diphenyl-7-hydroxy-2,4,10,12-tetraoxotridecane (22)

The above-described isomer mixture 21, in the amount produced, is dissolved in 35 ml of acetonitrile, and the solution is cooled to 0° C. 2.17 g (11 mmol) of tosyl azide are added to the cooled solution with stirring, and 2.0 g (20 mmol) of triethylamine are subsequently added dropwise at such a rate that the temperature does not exceed 5° C. The mixture is stirred at this temperature for 1 hour and subsequently at room temperature for 2 hours. 0.68 g (3.0 mmol) of 4-carboxyphenylsulfonyl azide is added to the mixture at 0° C., and the mixture is stirred for 30 minutes. After 1 hour at room temperature, the solvent is removed by distillation in vacuo, and the batch is kept at −20° C. overnight. The mixture is warmed to room temperature, the residue is taken up in dichloromethane, and the solution is washed three times with 100 ml of 15% strength aqueous potassium hydroxide solution in each case. The mixture is subsequently washed with water until neutral, and the organic phase is dried using magnesium sulfate. Evaporation leaves a black-red oil, which is substantially freed from solvent residues by applying a high vacuum. Column chromatography on silica gel using dichloromethane as eluent gives 1.2 g of virtually colorless product 22, which has the following composition.

$C_{30}H_{23}F_3N_4O_9S$ calc.: C 53.6% H 3.5% N 8.3% S 4.8%

(MW 672.6) found: C 53.9% H 3.8% N 8.0% S 4.7%

IR (KBr): 2,137 cm$^{-1}$ (C=N$_2$)

EXAMPLE 6

Preparation of a trifunctional ester of the general formula I containing two α-diazo-β-keto ester units and one sulfonate unit: the p-toluenesulfonate of 1,3-bis(5-diazo-4,6-dioxo-7-methyl-3-oxaoctyl)-5-(2-hydroxyethyl)-cyanuric acid (27)

Step 1:

1,3-bis[3-oxa-3-(tetrahydropyranyl)propyl]-5-(2-hydroxy-ethyl)cyanuric acid (23)

20.9 g (80 mmol) of 1,3,5-tris(2-hydroxyethyl)cyanuric acid are introduced, together with 20.2 g (0.24 mol) of 3,4-dihydro-2H-pyran, into 750 ml of dichloromethane. 4.02 g (16 mmol) of pyridinium toluene-4-sulfonate are added, and the mixture is stirred at room temperature for 5 hours. The solvent is subsequently removed by distillation in vacuo, and the evaporated mixture is taken up in ether. The solution is washed twice with 200 ml of semisaturated aqueous sodium chloride solution in each case and twice with 150 ml of water. Drying using magnesium sulfate and removal of the solvent by distillation in vacuo gives a virtually colorless residue, which contains, inter alia, the tetrahydropyranyl ether 23. 22 g of this compound are separated from the other products by column chromatography on silica gel using dichloromethane as eluent.

Step 2:

p-toluenesulfonate of 1,3-bis[3-oxa-3-(tetrahydropyranyl)propyl]-5-(2-hydroxyethyl)cyanuric acid (24)

8.59 g (20 mmol) of the above-described compound 23 are introduced, with 4.6 g (45 mmol) of N-methylmorpholine, into 50 ml of acetonitrile, and the mixture is cooled to 0° C. and stirred. After 30 minutes, 4.19 g (22 mmol) of p-toluenesulfonyl chloride are added to the solution. The mixture is stirred at 0° C. for 4 hours, and the solvent is removed by distillation in vacuo. 150 ml of water and 100 ml of dichloromethane are added to the oily residue which remains, and the organic phase is separated off. The aqueous phase is then extracted with dichloromethane, and the combined organic phases are washed three times with 150 ml of semisaturated potassium dihydrogen phosphate solution in each case. The mixture is subsequently washed with water until neutral and dried using sodium sulfate, and the solvent is removed by distillation in vacuo, leaving 10 g of a yellowish oil, which contains the protected sulfonate 24. The crude sulfonate 24 is reacted further without purification in the next step.

Step 3:

p-toluenesulfonate of 1,3,5-tris(2-hydroxyethyl)-cyanuric acid (25)

8.75 g (15 mmol) of the tetrahydropyranyl ether sulfonate 24 prepared in step 2 are introduced into 250 ml of a solvent mixture comprising acetic acid, tetrahydrofuran and water (3:2:1), and the mixture is stirred at 50° C. for 8 hours. Methanolic potassium hydroxide solution is subsequently added until the mixture is slightly alkaline (pH≈8 to 9). The solvent is removed by distillation in vacuo and the residue is taken up in 150 ml of dichloromethane. The solution is washed twice with 80 ml of semisaturated aqueous sodium chloride in each case and with 100 ml of water and dried using sodium sulfate, and the solvent is removed by distillation in vacuo, leaving a yellow-orange oil, which is separated by column chromatography on silica gel using dichloromethane/ethyl acetate as eluent, giving 4.3 g of a colorless oil 25, which crystallizes after a short time.

Step 4:

p-toluenesulfonate of 1,3-bis(4,6-dioxo-7-methyl-3-oxaoctyl)-5-(2-hydroxyethyl)cyanuric acid (26).

4.0 g (9.6 mmol) of the above-described compound 25 are introduced, with 4.11 g (19.2 mmol) of 5-(1-hydroxy-2-methylpropylidene)-2,2-dimethyl-1,3-dioxane-4,6-dione, into 20 ml of acetone, and the mixture is slowly warmed. Vigorous evolution of carbon dioxide commences from about 60° C. The solution is refluxed for 2.5 hours, and the solvent is removed by distillation in vacuo. The reaction mixture is cooled, leaving a dark red oil, which comprises virtually exclusively the desired β-keto ester/sulfonate 26, which is used without further purification as a starting material for the next step.

Step 5:

p-toluenesulfonate of 1,3-bis(5-diazo-4,6-dioxo-7-methyl-3-oxaoctyl)-5-(2-hydroxyethyl)cyanuric acid (27)

The above-described compound 26, in the amount produced, is dissolved in 50 ml of acetonitrile, and the solution is cooled to 0° C. 2.37 g (12 mmol) of tosyl azide are added to the cooled solution with stirring, and 2.5 g (25 mmol) of triethylamine are subsequently added dropwise at such a rate that the temperature does not exceed 5° C. The mixture is stirred at this temperature for 60 minutes, and subsequently warmed to room temperature. After 2 hours, tosyl azide is no longer detectable in the mixture by thin-layer chromatography (silica gel, dichloromethane as eluent). 1.70 g (7.5 mmol) of 4-carboxyphenylsulfonyl azide are added to the mixture at 0° C., and the mixture is stirred for 30 minutes. After a further 2 hours at room temperature, the solvent is removed by distillation in vacuo. The residue is taken up in dichloromethane, and the solution is washed three times with 200 ml of 10% aqueous potassium hydroxide solution in each case. The mixture is subsequently washed with water until neutral, and the organic phase is dried using sodium sulfate. Evaporation leaves a red oil, which is substantially freed from solvent residues by applying a high vacuum. Column chromatography on silica gel using dichloromethane/ethyl acetate as eluent gives 5.4 g of colorless α-diazo-β-keto ester/sulfonate 27, which has the following composition.

$C_{28}H_{33}N_7O_{12}S$ calc.: C 48.6% H 4.8% N 14.2% S 4.6%

(MW 691.7) found: C 49.0% H 4.9% N 13.2% S 4.6%

IR (KBr): 2,137 cm$^{-1}$ (C=N$_2$)

EXAMPLE 7

Preparation of a trifunctional ester of the general formula I containing two α-diazo-β-keto ester units and one sulfonate unit: the isopropylsulfonate of 1,1-bis[4-(6-diazo-1,4-dioxa-5,7-dioxononyl)phenyl]-1-[4-(3-hydroxy-1-oxapropyl)phenyl]ethane (30)

Step 1:

isopropylsulfonate of 1,1,1-tris[4-(3-hydroxy-1-oxapropyl)phenyl]ethane (28)

21.9 g (50 mmol) of 1,1,1-tris[4-(3-hydroxy-1-oxapropyl)-phenyl]ethane are introduced, with 10.6 g (105 mmol) of N-methylmorpholine, into 100 ml of acetonitrile, and the mixture is cooled to 0° C. and stirred. After 30 minutes, 7.56 g (53 mmol) of isopropylsulfonyl chloride are added to the solution. The mixture is stirred at 0° C. for 6 hours, and the mixture is kept at −20° C. overnight. After warming to room temperature, the solvent is removed by distillation in vacuo. 300 ml of water and 200 ml of dichloromethane are added to the oily residue which remains. The organic phase is separated off and the aqueous phase is then extracted with dichloromethane. The combined organic phases are washed three times with water until neutral and dried using sodium sulfate, and the solvent is removed by distillation in vacuo. Residues of the solvent are removed virtually completely by distillation in a high vacuum, leaving 26 g of yellow, viscous material, which contains the monosulfonate 28 as the main product. This is separated by preparative medium-pressure liquid chromatography on silica gel (eluent: petroleum ether/ethyl acetate), giving 14.6 g of colorless, crystalline monosulfonate 28.

Step 2:

isopropylsulfonate of 1,1-bis[4-(1,4-dioxa-5,7-dioxononyl)phenyl]-1-[4-(3-hydroxy-1-oxapropyl)phenyl]ethane (29)

2.5 g (4.6 mmol) of the above-described compound 28 are slowly warmed with 1.49 g (11.5 mmol) of methyl 3-oxovalerate, and the mixture is refluxed for 2.5 hours. The methanol formed and any methyl 3-oxovalerate still present are subsequently removed by distillation in vacuo. The reaction mixture is cooled, leaving a dark red oil, which comprises virtually exclusively the desired β-keto ester/sulfonate 29, which is used without further purification for the next step.

Step 3:

isopropylsulfonate of 1,1-bis[4-(6-diazo-1,4-dioxa-5,7-dioxononyl)phenyl]-1-[4-(3-hydroxy-1-oxapropyl)-phenyl]-ethane (30)

The above-described compound 29, in the amount produced in step 2, is dissolved in 50 ml of acetonitrile, and the solution is cooled to 0° C. 1.48 g (7.5 mmol) of tosyl azide are added to the cooled solution with stirring, and 1.5 g (15 mmol) of triethylamine are subsequently added. The mixture is stirred at this temperature for 1 hour and subsequently at room temperature for 2 hours. 0.39 g (1.7 mmol) of 4-carboxyphenylsulfonyl azide are added at 0° C., and the mixture is stirred for 30 minutes. After a further 2 hours at room temperature, the solvent is removed by distillation in vacuo. The residue is taken up in dichloromethane, and the solution is washed several times with 10% strength aqueous potassium hydroxide solution in each case. The mixture is subsequently washed with water until neutral, and the organic phase is dried using sodium sulfate. Evaporation leaves a black-red oil, which is substantially freed from solvent residues by applying a high vacuum. Column chromatography on silica gel using dichloromethane as eluent gives the virtually colorless product 30, which has the following composition.

$C_{39}H_{44}N_4O_{12}S$ calc.: C 59.1% H 5.6% N 7.1% S 4.0%

(MW 792.9) found: C 58.7% H 5.6% N 7.4% S 4.4%

IR (KBr): 2,138 cm$^{-1}$ (C=N$_2$)

EXAMPLE 8

Preparation of a trifunctional ester of the formula I containing two α-diazo-β-keto ester units and one sulfonate unit: the 3-phenylpropylsulfonate of 1,11-diadamantyl-2,10-diazo-4,8-dioxa-6-(hydroxymethyl)-6-methyl-1,3,9,11-tetraoxoundecane (35)

Step 1:

5-(hydroxymethyl)-2,2,5-trimethyl-1,3-dioxane (31)

1.0 g of p-toluenesulfonic acid is added to 96.2 g (0.80 mol) of 2-(hydroxymethyl)-2-methyl-1,3propanediol in 600 ml of acetone, and the mixture is heated to reflux. After 5 hours, the solution is neutralized while still hot by adding 3.0 g of potassium carbonate, and the mixture is stirred for a further 30 minutes and subsequently allowed to stand at room temperature overnight. The mixture is filtered through kieselguhr, and the solvent is removed by distillation in vacuo, leaving about 180 ml of a turbid, oily residue, which is purified by distillation in a high vacuum, giving 78 g of the alcohol 31 as a colorless, viscous oil.

Step 2:
3-phenylpropylsulfonate of 5-(hydroxymethyl)-2,2,5-trimethyl-1,3-dioxane (32)

10.4 g (65 mmol) of the partially protected alcohol 31 are introduced into 15.1 g (0.15 mol) of N-methylmorpholine, and the mixture is cooled to 0° C. and stirred. After 15 minutes, 14.3 g (70 mmol) of 3-phenylpropylsulfonyl chloride are added to the solution. The mixture is stirred at 0° C. for 4 hours, and the solvent is removed by distillation in vacuo. 500 ml of water and 250 ml of dichloromethane are added to the residue which remains. The organic phase is separated off and the aqueous phase is then extracted with dichloromethane. The combined organic phases are washed three times with 100 ml of semisaturated potassium dihydrogen phosphate solution in each case, washed with water until neutral and dried using sodium sulfate, and the solvent is removed by distillation in vacuo, leaving 14 g of a yellowish oil, which contains the desired sulfonate 32, which is used without further purification as a starting material for the next step.

Step 3:
3-phenylpropylsulfonate of 2-(hydroxymethyl)-2-methyl-1,3-propanediol (33)

10.0 g (30.4 mmol) of the protected sulfonate 32 prepared in step 2 are introduced into 250 ml of methanol. 3 N hydrochloric acid is added dropwise until the pH is less than 5. 0.40 g of p-toluenesulfonic acid is subsequently added, the mixture is stirred at room temperature for 6 hours, and methanolic potassium hydroxide solution is added until the mixture is slightly alkaline (pH$\approx$8 to 9). The solvent is removed by distillation in vacuo, and the residue which remains is separated by column chromatography on silica gel using dichloromethane as eluent, giving 5.4 g of a colorless oil 33, which crystallizes after a few hours.

Step 4:
3-phenylpropylsulfonate of 1,11-diadamantyl-4,8-dioxa-6-(hydroxymethyl)-6-methyl-1,3,9,11-tetraoxoundecane (34)

3.1 g (10.7 mmol) of the above-described compound 33 are introduced, with 6.59 g (21.5 mmol) of 5-(1-adamantyl-1-hydroxymethylidene)-2,2-dimethyl-1,3-dioxane-4,6-dione, into 35 ml of acetone, and the mixture is slowly warmed. Vigorous evolution of carbon dioxide commences from about 0° C. The solution is refluxed for 2.5 hours, and the solvent is subsequently removed by distillation in vacuo. The reaction mixture is cooled, leaving an oily residue, which contains the dark red $\beta$-keto ester/sulfonate 34 and is employed without further purification in the next step.

Step 5:
3-phenylpropylsulfonate of 1,11-diadamantyl-2,10-diazo-4,8-dioxa-6-(hydroxymethyl)-6-methyl-1,3,9,11-tetraoxoundecane (35)

The above-described compound 34, in the amount produced in step 4, is dissolved in 50 ml of acetonitrile and 10 ml of acetone, and the solution is cooled to 0° C. 2.76 g (14 mmol) of tosyl azide are added to the cooled solution with stirring, and 2.5 g (25 mmol) of triethylamine are subsequently added dropwise at such a rate that the temperature does not exceed 5° C. The mixture is stirred at this temperature for 1 hour and subsequently warmed to room temperature. After 2 hours, 1.70 g (7.5 mmol) of 4-carboxyphenylsulfonyl azide are added at 0° C., and the mixture is stirred for 15 minutes. After a further 2 hours at room temperature, the solvent is removed by distillation in vacuo. The residue is taken up in dichloromethane, and the solution is washed three times with 100 ml of 15% strength aqueous potassium hydroxide solution in each case. The mixture is subsequently washed with water until neutral, and the organic phase is dried using sodium sulfate. Evaporation leaves an orange-red oil, which is substantially freed from solvent residues by applying a high vacuum. Column chromatography on silica gel using dichloromethane as eluent gives 1.2 g of virtually colorless $\alpha$-diazo-$\beta$-keto ester/sulfonate 35, which has the following composition.

$C_{39}H_{48}N_4O_9S$ calc.: C 62.6% H 6.5% N 7.5% S 4.3%
(MW 748.9) found: C 62.3% H 6.3% N 7.2% S 4.4%
IR (KBr): 2,137 cm$^{-1}$ (C=N$_2$)

EXAMPLE 9

Preparation of a trifunctional ester of the general formula I containing two $\alpha$-diazo-$\beta$-keto ester units and one sulfonate unit: the 4-cyanophenylsulfonate of 8,16-diazo-2,5,10,14,19,22-hexoxa-12-(hydroxymethyl)-12-methyl-7,9,15,17-tetraoxotrieicosane (39)

Step 1:
5-(hydroxymethyl)-2,2,5-trimethyl-1,3-dioxane (31)
Preparation see Example 8, step 1

Step 2:
4-cyanophenylsulfonate of 5-(hydroxymethyl)-2,2,5-trimethyl-1,3-dioxane (36)

5.77 g (36 mmol) of the above-described compound 31 are introduced into 10.1 g (0.10 mol) of N-methylmorpholine, and the mixture is cooled to 0° C. and stirred. After 10 minutes, 8.07 g (40 mmol) of 4-cyanophenylsulfonyl chloride are added to the solution. The mixture is stirred at 0° C. for 5 hours, and 250 ml of water and 150 ml of dichloromethane are added. The organic phase is separated off and the aqueous phase is then extracted with dichloromethane. The combined organic phases are washed three times with 100 ml of semisaturated potassium dihydrogen phosphate solution in each case, washed with water until neutral and dried using sodium sulfate, and the solvent is removed by distillation in vacuo, leaving 9.8 g of pale yellowish crystals, which comprise virtually exclusively the desired sulfonate 36, which is used without further purification as a starting material for the next step.

Step 3:
4-cyanophenylsulfonate of 2-(hydroxymethyl)-2-methyl-1,3-propanediol (37)

9.76 g (30 mmol) of the protected sulfonate 36 prepared in step 2 are introduced into 150 ml of methanol, and 3 N hydrochloric acid is added dropwise until the pH is less than 5. 0.50 g of p-toluenesulfonic acid is subsequently added, the mixture is stirred at room temperature for 4.5 hours, and methanolic potassium hydroxide solution is added until the mixture is slightly alkaline (pH $\approx$8 to 9). The solvent is removed by distillation in vacuo, and the residue which remains is separated by column chromatography on silica gel using dichloromethane as eluent, giving 5.2 g of crystalline product 37.

Step 4:
4-cyanophenylsulfonate of 2,5,10,14,19,22-hexoxa-12-(hydroxymethyl)-12-methyl-7,9,15,17-tetraoxotrieicosane (38)

2.85 g (10.0 mmol) of the above-described compound 37 are introduced, with 5.21 g (20.0 mmol) of 5-(3,6-dioxa-1-hydroxyheptylidene)-2,2-dimethyl-1,3-dioxane-4,6-dione, into 20 ml of acetone, and the mixture is slowly warmed. Vigorous evolution of carbon dioxide commences from about 60° C. The solution is refluxed for 2.5 hours, and the solvent is subsequently removed by distillation. The reaction mixture is cooled, leaving a black-brown oil, which contains the β-keto ester/sulfonate 38 as the main product, which is employed without further purification in step 5.

Step 5:
4-cyanophenylsulfonate of 8,16-diazo-2,5,10,14,19,22-hexoxa-12-(hydroxymethyl)-12-methyl-7,9,15,17-tetraoxotrieicosane (39)

The above-described compound 38, in the amount produced, is dissolved in 50 ml of acetonitrile, and the solution is cooled to 0° C. 2.37 g (12 mmol) of tosyl azide are added to the cooled solution with stirring, and 2.5 g (25 mmol) of triethylamine are subsequently added dropwise at such a rate that the temperature does not exceed 5° C. The mixture is stirred at this temperature for 1 hour and subsequently warmed to room temperature. After 2 hours, tosyl azide is no longer detectable in the mixture by thin-layer chromatography (silica gel, dichloromethane as eluent). 1.82 g (8.0 mmol) of 4-carboxyphenylsulfonyl azide are added to the mixture at 0° C., and the mixture is stirred for 30 minutes. After a further 2 hours at room temperature, the solvent is removed by distillation in vacuo, and the residue is taken up in dichloromethane. The solution is washed three times with 100 ml of 10% strength aqueous potassium hydroxide solution in each case and three times with 80 ml of water in each case, the organic phase is dried using sodium sulfate, and the solvent is removed by distillation in vacuo, leaving a red oil, which is substantially freed from solvent residues by applying a high vacuum. Column chromatography on silica gel using dichloromethane as eluent gives the virtually colorless α-diazo-β-keto ester/sulfonate 39, which has the following composition.

$C_{26}H_{31}N_5O_{13}S$ calc.: C 47.8% H 4.8% N 10.7% S 4.9%

(MW 653.6) found: C 48.2% H 4.8% N 10.8% S 4.6%

IR (KBr): 2,143 cm$^{-1}$ (C=N$_2$)

EXAMPLE 10

Preparation of a pentafunctional ester of the general formula I containing four α-diazo-β-keto ester units and one sulfonate unit: the 4-bromophenylsulfonate of 1,2,10,11-tetra(4-cyclohexyl-3-diazo-2,4-dioxo-1-oxabutyl)triglycerol (43)

Step 1:
4-bromophenylsulfonate of 1,2,10,11-O,O-di(isopropylidene)triglycerol (40)

20.0 g (62.4 mmol) of commercially available O,O-di(isopropylidene)triglycerol are introduced into 25.2 g (0.32 mol) of pyridine, and the mixture is cooled to 0° C. and stirred. After 20 minutes, 22.4 g (87.6 mmol) of 4-bromophenylsulfonyl chloride are added to the solution. The mixture is stirred at 0° C. for 4 hours and at room temperature for 30 minutes. The precipitate formed is filtered off, washed several times with water and taken up in 300 ml of dichloromethane. The organic phase is separated off, the aqueous phase is then extracted with dichloromethane, and the combined organic phases are washed four times with 200 ml of semisaturated potassium dihydrogen phosphate solution in each case. The mixture is subsequently washed with water until neutral and dried using sodium sulfate, and the solvent is removed by distillation in vacuo, leaving 29 g of a yellow oil, which partially crystallizes and comprises virtually exclusively the sulfonate 40, which is used without further purification as a starting material for the next step.

Step 2:
4-bromophenylsulfonate of triglycerol (41)

14 g (26 mmol) of the protected triglycerol sulfonate 40 prepared in step 1 are introduced into 80 ml of methanol, and 3 N hydrochloric acid is added dropwise until the pH is less than 5. 0.35 g of p-toluenesulfonic acid is subsequently added, the mixture is stirred at room temperature for 16 hours, and methanolic potassium hydroxide solution is added until the mixture is slightly alkaline (pH ≈ 8 to 9). The solvent is removed by distillation in vacuo, leaving an oil, which is separated by column chromatography on silica gel using dichloromethane/ethyl acetate as eluent, giving 9.8 g of triglycerol 6-sulfonate 41 as a colorless oil.

Step 3:
4-bromophenylsulfonate of 1,2,10,11-tetra(4-cyclohexyl-2,4-dioxo-1-oxabutyl)triglycerol (42)

3.2 g (7.0 mmol) of the above-described triglycerol 6-sulfonate 41 are slowly warmed with 7.7 g (42 mmol) of methyl 3-cyclohexyl-3oxopropionate. The homogeneous mixture is refluxed for 2 hours, and the methanol formed and any methyl 3-cyclohexyl-3-oxopropionate still present are removed by distillation in vacuo. The reaction mixture is cooled, leaving a black-brown, viscous oil, which contains the β-keto ester/sulfonate 42, which is employed without further purification in step 4.

Step 4:
4-bromophenylsulfonate of 1,2,10,11-tetra(4-cyclohexyl-3-diazo-2,4-dioxo-1-oxabutyl)triglycerol (43)

The above-described compound 42, in the amounts produced, is dissolved in 80 ml of acetonitrile, and the solution is cooled to 0° C. 3.94 g (20 mmol) of tosyl azide are added to the cooled solution with stirring, and 3.5 g (35 mmol) of triethylamine are subsequently added dropwise at such a rate that the temperature does not exceed 5° C. The mixture is stirred at this temperature for 45 minutes and subsequently warmed to room temperature. After 1.5 hours, tosyl azide is no longer detectable in the mixture by thin-layer chromatography (silica gel, dichloromethane as eluent). 1.82 g (8.0 mmol) of 4-carboxyphenyl sulfonyl azide are added to the mixture at 0° C., and the mixture is stirred for 45 minutes. After a further 1.5 hours at room temperature, the solvent is removed by distillation in vacuo. The residue is taken up in dichloromethane, and the solution is washed three times with 100 ml of 15% strength aqueous potassium hydroxide solution in each case. The mixture is subsequently washed with water until neutral, and the organic phase is dried using sodium sulfate. Evaporation leaves a dark red oil, which is substantially freed from solvent residues by applying a high vacuum. Column chromatography on silica gel using dichloromethane as eluent gives 4.2 g of virtually colorless product 43, which has the following composition.

$C_{51}H_{63}BrN_8O_{17}S$ calc.: C 52.3% H 5.4% N 9.6% S 2.7%

(MW 1172.1) found: C 51.9% H 5.6% N 9.1% S 2.4%

IR (KBr): 2,138 cm$^{-1}$ (C=N$_2$)

EXAMPLE 11

Preparation of an isomeric mixture of two pentafunctional esters of the formula I each containing four α-diazo-β-keto ester units and one sulfonate unit: the n-propylsulfonate of 2-hydroxy-1,1,3,3-tetra(4-diazo-5- cyclohexyl-3,5-dioxo-2-oxapentyl)cyclohexane and of 2-(3-diazo-4-cyclohexyl-2,4-dioxo-1-oxabutyl)-1-(hydroxymethyl)-1,3,3-tris(4-diazo-5-cyclohexyl-3,5-dioxo-2-oxapentyl)cyclohexane (48)

Step 1:

isomeric O,O-diisopropylidene acetals of 2-hydroxy-1,1,3,3-tetra(hydroxymethyl)cyclohexane (44)

0.45 g of p-toluenesulfonic acid is added to 16.2 g (73.5 mmol) of 2-hydroxy-1,1,3,3-tetra(hydroxymethyl)cyclohexane in 120 ml of acetone, and the mixture is heated to reflux. After 5.5 hours, the solution is neutralized while still hot by adding 1.35 g of potassium carbonate, and the mixture is stirred for a further 40 minutes and then left to stand at room temperature overnight. The mixture is filtered through kieselguhr, and the solvent is removed by distillation in vacuo, leaving about 35 ml of an oily residue, which is purified by distillation in a high vacuum, giving 13.2 g of a mixture of the isomeric alcohols 44 as a colorless oil.

Step 2:

n-propylsulfonates of the isomeric O,O-diisopropylidene acetals of 2-hydroxy-1,1,3,3-tetra(hydroxymethyl)cyclohexane (45)

6.0 g (20 mmol) of the above-described isomeric mixture 44 are introduced into 12.1 g (0.12 mol) of N-methylmorpholine, and the mixture is cooled to 0° C. and stirred. After 15 minutes, 3.42 g (24 mmol) of n-propylsulfonyl chloride are added to the solution. The mixture is stirred at 0° C. for 3.5 hours, and 150 ml of ice water and 100 ml of dichloromethane are added. The organic phase is separated off and the aqueous phase is then extracted with dichloromethane. The combined organic phases are washed five times with 100 ml of water in each case and dried using sodium sulfate, and the solvent is removed by distillation in vacuo, leaving 4.3 g of a dirty-yellow oil, which contains the isomeric sulfonates 45. The crude product is used without further purification as a starting material for step 3.

Step 3:

isomeric n-propylsulfonates of 2-hydroxy-1,1,3,3-tetra(hydroxymethyl)cyclohexane (46)

4.3 g (10.6 mmol) of the isomeric sulfonates 45 prepared in step 2 are introduced into 100 ml of methanol, and 3 N hydrochloric acid is added dropwise until the pH is less than 5. 0.65 g of p-toluenesulfonic acid is subsequently added, the mixture is stirred at room temperature for 3.5 hours, and methanolic potassium hydroxide solution is added until the mixture is slightly alkaline (pH≈8 to 9). The solvent is removed by distillation in vacuo, leaving a yellow oil. Column chromatography on silica gel using dichloromethane/ethyl acetate as eluent gives 3.0 g of a colorless oil 46.

Step 4:

n-propylsulfonates of 2-hydroxy-1,1,3,3-tetra(5-cyclohexyl-3,5-dioxo-2-oxapentyl)cyclohexane and of 2-(4-cyclohexyl-2,4-dioxo-1-oxabutyl)-1-(hydroxymethyl)-1,3,3-tris(5-cyclohexyl-3,5-dioxo-2-oxapentyl)cyclohexane (47)

1.5 g (4.6 mmol) of the isomeric sulfonates 46 are introduced, with 4.67 g (18.4 mmol) of 5-(1-cyclohexyl-1-hydroxymethylidene)-2,2-dimethyl-1,3-dioxane-4,6-dione, into 20 ml of acetone, and the mixture is slowly warmed. Vigorous evolution of carbon dioxide commences from about 60° C. The solution is refluxed for 2 hours, and the solvent is subsequently removed by distillation in vacuo. The reaction mixture is cooled, leaving a black-brown oil, which comprises virtually exclusively the desired β-keto ester/sulfonates 47. This isomer mixture is used without further purification as a starting material for the next step.

Step 5:

n-propylsulfonates of 2-hydroxy-1,1,3,3-tetra)4-diazo-5-cyclohexyl-3,5-dioxo-2-oxapentyl)cyclohexane and of 2-(3-diazo-4-cyclohexyl-2,4-dioxo-1-oxabutyl)-1-(hydroxymethyl)-1,3,3-tris(4-diazo-5-cyclohexyl-3,5dioxo-2-oxapentyl)cyclohexane (48)

The above-described isomer mixture 47, in the amount produced, is dissolved in 40 ml of acetonitrile, and the solution is cooled to 0° C. 2.96 g (15 mmol) of tosyl azide are added to the cooled solution with stirring, and 2.8 g (28 mmol) of triethylamine are subsequently added dropwise. The mixture is stirred at this temperature for 1 hour and subsequently at room temperature for 2 hours. 1.0 g (4.4 mmol) of 4-carboxyphenylsulfonyl azide is added at 0° C., and the mixture is stirred for 45 minutes. After 1.5 hours at room temperature, the solvent is removed by distillation in vacuo, and the batch is kept at −20° C. overnight. The mixture is warmed to room temperature, and the residue is taken up in dichloromethane and washed three times with 120 ml of 15% strength aqueous potassium hydroxide solution in each case. The mixture is subsequently washed with water until neutral, and the organic phase is dried using sodium sulfate. Evaporation leaves a dark red oil, which is substantially freed from solvent residues by applying a high vacuum. Column chromatography on silica gel using dichloromethane as eluent gives 1.9 g of the isomeric α-diazo-β-keto ester/sulfonates 48 as a virtually colorless product which has the following composition.

$C_{49}H_{66}N_8O_{15}S$ calc.: C 56.6% H 6.4% N 10.8% S 3.1%

(MW 1039.2) found: C 57.0% H 6.5% N 10.1% 3.4%

IR (KBr): 2,138 cm$^{-1}$ (C=N$_2$)

EXAMPLE 12

Preparation of a hexafunctional ester of the general formula I containing four α-diazo-β-keto ester units and two sulfonate units: the 6,10-bis(phenylsulfonate) of 1,2,14,15-tetra(4-tert-butyl-3-diazo-2,4-dioxo-1-oxabutyl)tetraglycerol (52)

Step 1:

6,10-bis(phenylsulfonate) of 1,2,14,15-O,O-di(isopropylidene)tetraglycerol (49)

12.5 g (31.7 mmol) of commercially available 1,2,14,15-O,O-di(isopropylidene)tetraglycerol are introduced into 32 g (0.32 mol) of N-methylmorpholine, and the mixture is cooled to 0° C. and stirred. After 30 minutes, 11.8 g (67 mmol) of phenylsulfonyl chloride are added to the solution. The mixture is stirred at 0° C. for 8 hours and at room temperature for 30 minutes, and 300 ml of ice water and 200 ml of dichloromethane are added to the suspension. The organic phase is separated off, the aqueous phase is then extracted with dichloromethane and the combined organic phases are washed twice with 150 ml of semisaturated potassium dihydrogen phosphate solution in each case. The mixture is subsequently washed with water until neutral and dried using sodium sulfate, and the solvent is removed by distillation in vacuo, leaving 14 g of a yellow-brown oil which contains the protected tetraglycerol 6,10-bis(sulfonate) 49, which is used without further purification in step 2.

Step 2:

6,10-bis(phenylsulfonate) of tetraglycerol (50)

11.8 g (17.5 mmol) of the protected tetraglycerol 49 prepared in step 1 are introduced into 180 ml of methanol, and 3 N hydrochloric acid is added dropwise until the pH is less than 5. 0.65 g of p-toluenesulfonic acid is subsequently added, the mixture is stirred at room temperature for 14 hours, and methanolic potassium hydroxide solution is added until the mixture is slightly alkaline (pH≈8 to 9). The solvent is removed by distillation in vacuo, leaving an oil, which is separated by column chromatography on silica gel using dichloromethane/ethyl acetate as eluent, giving 5.1 g of tetraglycerol 6,10-bis(sulfonate) 50 as a colorless oil.

Step 3:

6,10-bis(phenylsulfonate) of 1,2,14,15-tetra(4-t-butyl-2,4-dioxo-1-oxabutyl)tetraglycerol (51)

2.6 g (4.4 mmol) of the above-described tetraglycerol 6,10-bis(sulfonate) 50 are introduced, with 4.0 g (17.6 mmol) of 5-(2,2-dimethyl-1-hydroxypropylidene)-2,2-dimethyl-1,3-dioxane-4,6-dione, into 30 ml of acetone, and the mixture is slowly warmed. Vigorous evolution of carbon dioxide commences from about 60° C. The homogeneous mixture is refluxed for 2.5 hours, and the solvent is subsequently removed by distillation in vacuo. The reaction mixture is cooled, leaving a black-red, viscous oil, which contains the β-keto ester/sulfonate 51, which is employed without further purification in step 4.

Step 4:

6,10-bis(Phenylsulfonate) of 1,2,14,15-tetra(4-t-butyl-3-diazo-2,4-dioxo-1-oxabutyl)tetraglycerol (52)

The above-described compound 51, in the amount produced, is dissolved in 80 ml of acetonitrile, and the mixture is cooled to 0° C. 2.56 g (13 mmol) of tosyl azide are added to the cooled solution with stirring, and 4.0 g (40 mmol) of triethylamine are subsequently added dropwise at such a rate that the temperature does not exceed 5° C. The mixture is stirred at this temperature for 1 hour and subsequently at room temperature for 2 hours. 1.14 g (5.0 mmol) of 4-carboxyphenylsulfonyl azide are subsequently added at 0° C., and the mixture is stirred for 1.5 hours. After a further 1.5 hours at room temperature, the solvent is removed by distillation in vacuo, and the residue is taken up in dichloromethane. The solution is washed three times with 80 ml of 20% strength aqueous potassium hydroxide solution in each case and four times with 60 ml of water in each case until neutral. Drying using sodium sulfate and removal of the solvent by distillation gives a dark red oil, which is substantially freed from solvent residues by applying a high vacuum. Column chromatography on silica gel using dichloromethane as eluent gives 2.3 g of α-diazo-β-keto ester/sulfonate 52, which has the following composition.

$C_{52}H_{66}N_8O_{21}S_2$ calc.: C 51.9% H 5.5% N 9.3% S 5.3%

(MW 1203.3) found: C 52.3% H 5.7% N 8.6% S 5.4%

IR (KBr): 2,136 cm$^{-1}$ (C=N$_2$)

EXAMPLES 13-72

Further compounds of the general formula I are presented which were prepared analogously to the examples described above. Due to the large number of compounds, these are characterized in the table below with respect to the variation possibilities described in the formula I. As an analytical value, the quantitative determination of the nitrogen provides sufficient information.

| No. | R$^1$ | R$^2$ | X | m | n | % of N calc./found |
|---|---|---|---|---|---|---|
| 13 | tBu— | pCH$_3$—C$_6$H$_4$— | —CH$_2$—CH—CH$_2$— | 3 | 1 | 10.18/10.4 |
| 14 | C$_6$H$_{11}$— | Ph— | " | 3 | 1 | 9.52/9.5 |
| 15 | CH$_3$OCC$_2$H$_4$— (O=) | pBr—C$_6$H$_4$— | " | 3 | 1 | 8.30/8.1 |
| 16 | CH$_3$CC$_2$H$_4$— (O=) | oNO$_2$—C$_6$H$_4$— | " | 3 | 1 | 11.49/11.7 |
| 17 | PhCH$_2$OCH$_2$— | iPr— | " | 3 | 1 | 8.88/8.6 |
| 18 | C$_6$H$_{11}$— | pCH$_3$—C$_6$H$_4$— | CH$_3$C(CH$_2$)$_3$— | 3 | 1 | 8.88/8.8 |
| 19 | nBu— | nBu— | " | 3 | 1 | 10.29/10.3 |
| 20 | tBu— | Cl(CH$_2$)$_3$— | " | 3 | 1 | 9.92/9.7 |
| 21 | nC$_8$H$_{17}$— | iPr— | " | 3 | 1 | 8.72/8.6 |
| 22 | Ph(CH$_2$)$_2$— | pNO$_2$—C$_6$H$_4$— | " | 3 | 1 | 11.66/11.3 |
| 23 | C$_6$H$_{11}$— | CH$_3$SO$_2$CH$_2$— | " | 3 | 1 | 8.86/8.7 |
| 24 | tBu— | pBr—C$_6$H$_4$— | " | 3 | 1 | 8.71/8.9 |
| 25 | C$_6$H$_{11}$— | pCH$_3$—C$_6$H$_4$— | CH$_3$CH$_2$C(CH$_2$)$_3$— | 3 | 1 | 8.69/8.8 |
| 26 | C$_6$H$_{11}$— | pBr—C$_6$H$_4$— | " | 3 | 1 | 7.90/7.9 |
| 27 | C$_6$H$_{11}$— | pCF$_3$—C$_6$H$_4$— | " | 3 | 1 | 8.02/8.3 |

-continued

| No. | R¹ | R² | X | m | n | % of N calc./found |
|---|---|---|---|---|---|---|
| 28 | $C_6H_{11}-$ | 4-(CH₃C(O)NH)-2-Cl-C₆H₃— | " | 3 | 1 | 9.70/9.7 |
| 29 | tBu— | PhCH₂— | " | 3 | 1 | 9.45/9.5 |
| 30 | $CH_3OC(O)C_2H_4-$ | 4-(CH₃C(O)NH)-C₆H₄— | " | 3 | 1 | 10.07/10.0 |
| 31 | nBu— | pCH₃—C₆H₄— | $-N(CH_2CH_2)_3-$ | 3 | 1 | 12.38/12.5 |
| 32 | iBu— | pCN—C₆H₄— | " | 3 | 1 | 14.58/14.2 |
| 33 | phthalimidomethyl (N-CH₂— of phthalimide) | PhCH₂— | cyclohexyl-NHC(O)NH—C(CH₂)₃— | 3 | 1 | 12.30/12.1 |
| 34 | $nC_8H_{17}-$ | p(tBu)—C₆H₄— | cyclohexyl-NHC(O)NH—C(CH₂)₃— | 3 | 1 | 9.78/9.6 |
| 35 | $CH_3O(CH_2)_2OCH_2-$ | Cl₃C— | " | 3 | 1 | 10.56/10.6 |
| 36 | $PhCH_2OC(O)NHCH_2-$ | H₃C— | " | 3 | 1 | 12.30/12.1 |
| 37 | $nC_8H_{17}-$ | Ph— | " | 3 | 1 | 10.55/10.3 |
| 38 | $nC_{17}H_{35}-$ | pCF₃—C₆H₄— | " | 3 | 1 | 7.52/7.6 |
| 39 | Ph(CH₂)₂— | H₃C— | " | 3 | 1 | 11.69/11.8 |
| 40 | $EtOC(O)(CH_2)_3-$ | p(tBu)—C₆H₄— | " | 3 | 1 | 9.81/9.7 |
| 41 | $nC_{10}H_{21}-$ | oNO₂—C₆H₄— | " | 3 | 1 | 10.92/10.6 |
| 42 | tBu— | pCH₃—C₆H₄— | 1,3,5-tris[(CH₂)₂—]isocyanurate | 3 | 1 | 13.62/13.5 |
| 43 | $C_6H_{11}-$ | Ph— | " | 3 | 1 | 12.94/12.7 |
| 44 | $C_4H_7-$ | H₃C— | " | 3 | 1 | 15.33/14.9 |
| 45 | $PhCH_2OC(O)NHCH_2-$ | p(tBu)—C₆H₄— | " | 3 | 1 | 12.92/12.9 |
| 46 | $nC_6H_{13}-$ | pCF₃—C₆H₄— | CH₃C[(OC₂H₄)₃—]₃ (1,1,1-tris) | 3 | 1 | 5.84/5.9 |
| 47 | PhOCH₂— | oNO₂—C₆H₄— | " | 3 | 1 | 7.15/7.2 |
| 48 | $C_6H_{11}-$ | Cl(CH₂)₃— | " | 3 | 1 | 6.31/6.3 |
| 49 | $CH_3O(CH_2)_2OCH_2-$ | Ph— | " | 3 | 1 | 6.23/6.0 |

-continued
| No. | R¹ | R² | X | m | n | % of N calc./found |
|---|---|---|---|---|---|---|
| 50 | $C_6H_{11}-$ | nBu— | 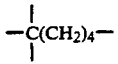 | 4 | 1 | 10.63/10.4 |
| 51 | $PhOCH_2-$ | $CH_3SO_2CH_2-$ | " | 4 | 1 | 9.35/9.7 |
| 52 | $PhCH_2-$ | $pCH_3-C_6H_4-$ | " | 4 | 1 | 9.90/10.2 |
| 53 | $C_6H_{11}-$ | 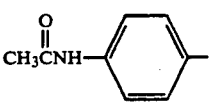 | 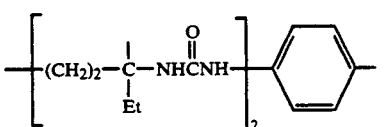 | 4 | 1 | 13.63/13.5 |
| 54 | $Ph(CH_2)_2-$ | 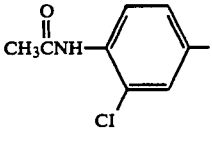 | 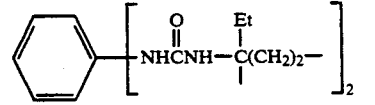 | 4 | 1 | 12.52/12.5 |
| 55 | tBu— | $p(tBu)-C_6H_4-$ | 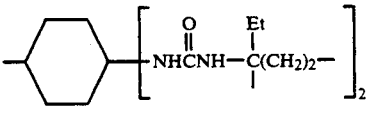 | 4 | 1 | 13.25/13.2 |
| 56 | $nC_8H_{17}-$ | pH | " | 4 | 1 | 11.98/11.8 |
| 57 | $PhCH_2OCH_2-$ | $pCN-C_6H_4-$ | 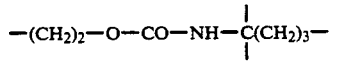 | 4 | 1 | 10.95/10.7 |
| 58 | $C_6H_{11}-$ | $pNO_2-C_6H_4-$ | " | 4 | 1 | 12.06/12.0 |
| 59 | 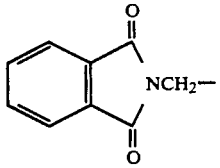 | $pBr-C_6H_4-$ | $-(CH_2)_2N-CH_2CH_2-N(CH_2)_2-$ | 4 | 1 | 12.59/12.2 |
| 60 | iBu— | $pCF_3-C_6H_4-$ | " | 4 | 1 | 12.44/12.3 |
| 61 | $C_6H_{11}-$ | $Cl(CH_2)_3-$ | 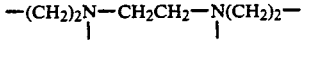 | 5 | 1 | 10.44/10.1 |
| 62 | tBu— | $pCH_3-C_6H_4-$ | " | 5 | 1 | 10.40/11.0 |
| 63 | $PhOCH_2-$ | $H_3C-$ | " | 5 | 1 | 10.12/10.5 |
| 64 | $C_6H_{11}-$ | Ph— | 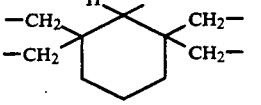 | 5 | 1 | 10.25/10.5 |
| 65 | $C_6H_{11}-$ | $pCH_3-C_6H_4-$ | " | 5 | 1 | 10.12/10.1 |
| 66 | $C_6H_{11}-$ | 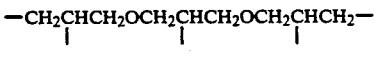 | " | 5 | 1 | 10.23/9.8 |
| 67 | $C_6H_{11}-$ | $H_3C-$ | 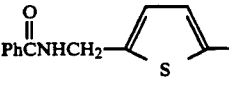 | 6 | 2 | 9.98/10.1 |
| 68 | tBu— | $H_3C-$ | " | 6 | 2 | 11.00/11.0 |

-continued

| No. | R¹ | R² | X | m | n | % of N calc./found |
|---|---|---|---|---|---|---|
| 69 | $C_6H_{11}$— | $pCH_3$—$C_6H_4$— | —$CH_2CHCH_2(OCH_2CHCH_2)_2OCH_2CHCH_2$— | 6 | 2 | 8.49/8.2 |
| 70 | $C_6H_{11}$— | pBr—$C_6H_4$— | (see structure) | 8 | 2 | 9.81/9.6 |
| 71 | $C_6H_{11}$— | iPr— | (see structure) | 8 | 2 | 11,30/11,0 |
| 72 | $pCF_3$ | $pCF_3$—$C_6H_4$— | " | 8 | 3 | 7,76/7,4 | o = ortho (1,2-disubstituted)
p = para (1,4-disubstituted)
n = unbranched alkyl chain
i = iso-branched alkyl chain
t = tertiary-branched alkyl chain
Et = ethyl
Bu = butyl
Pr = propyl
Ph = phenyl
$C_6H_{11}$ = cyclohexyl
$C_4H_7$ = cyclobutyl The products from Examples 1 to 12, the compounds 5, 9, 13, 17, 22, 27, 30, 35, 39, 43, 48 and 52, are shown below as pictorial formulae.

Example 1, Compound 5

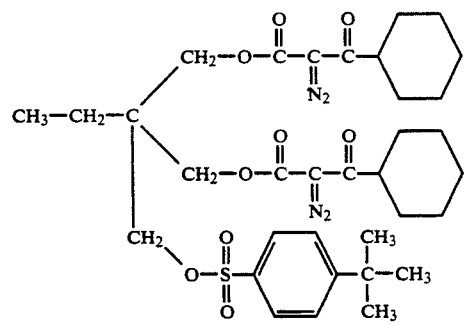

Example 2, Compound 9

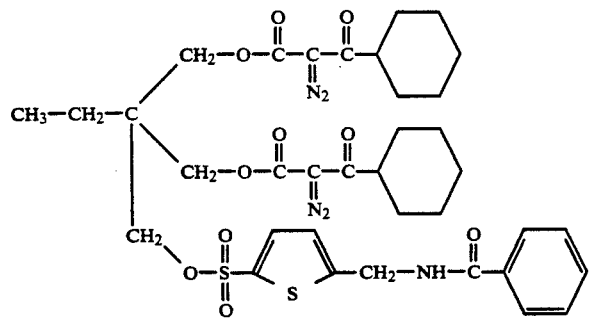

Example 3, Compound 13

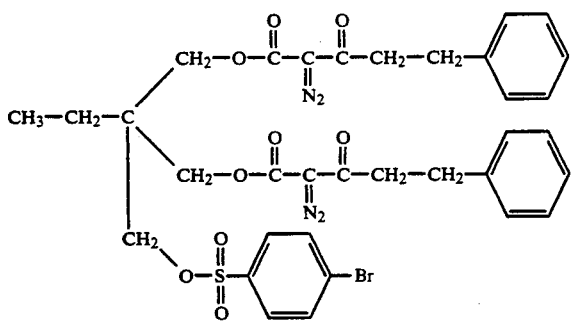
Example 4, Compound 17
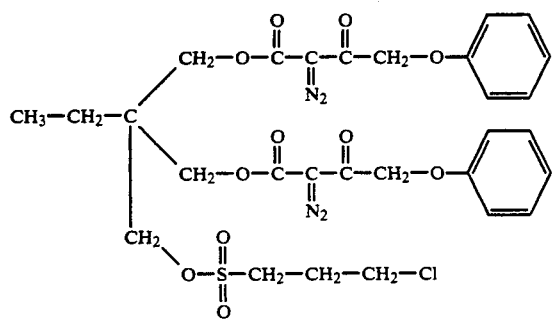
Example 5, Compounds 22
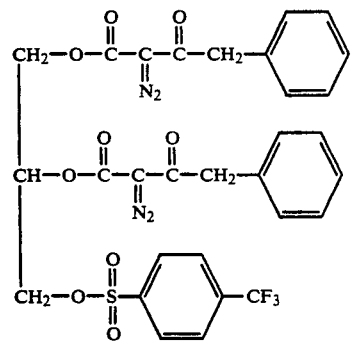
Isomeric mixture
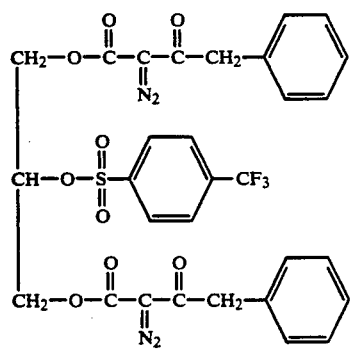
Example 6, Compound 27

-continued
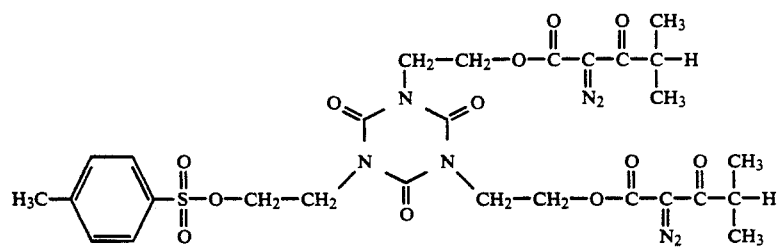
Example 7, Compound 30
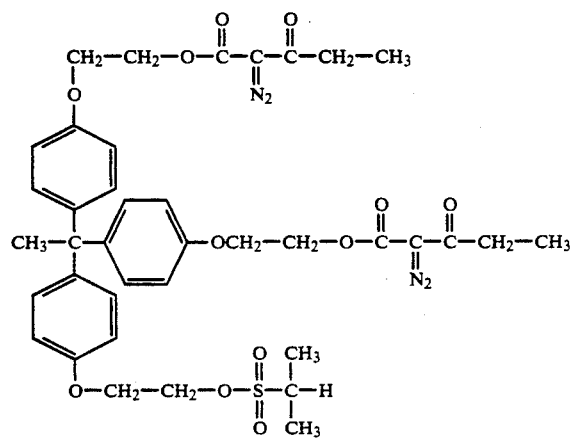
Example 8, Compound 35
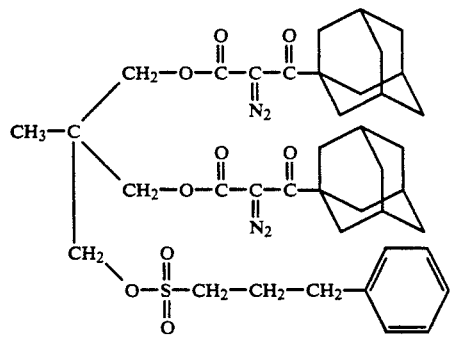
Example 9, Compound 39
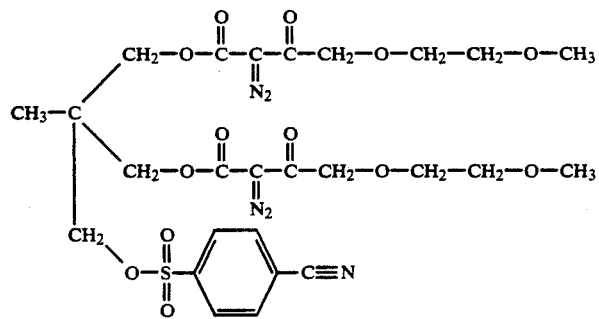
Example 10, Compound 43

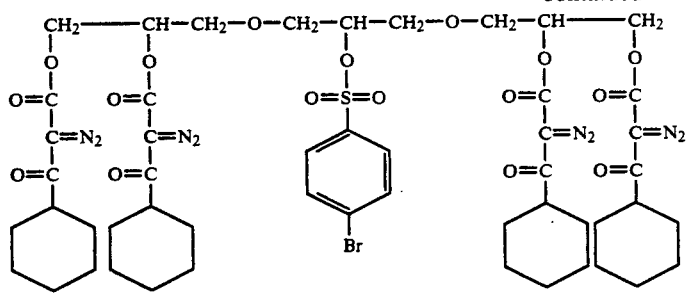

Example 11, Compounds 48

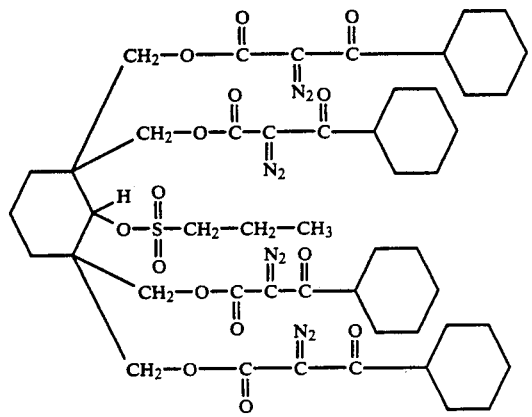

Isomeric mixture

Example 12, Compound 52

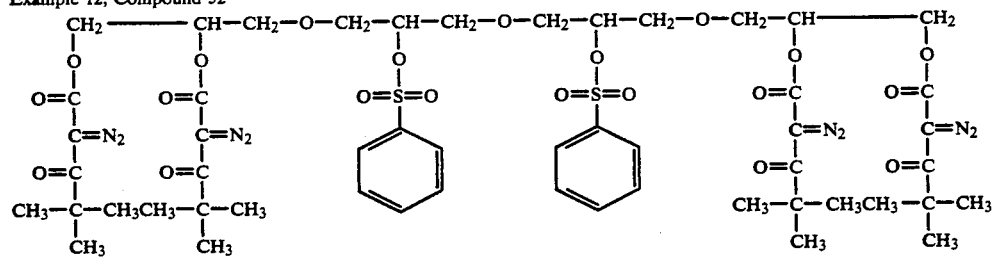

EXAMPLE 73

(Comparative Example)

9.62 g (80 mmol) of 2-(hydroxymethyl)-2-methyl-1,3-propanediol are converted analogously to Example 9 (step 4) into a trifunctional β-keto ester (compound 53), but in this case using 62.5 g (0.24 mol) of 5-(3,6-dioxa-1-hydroxyheptylidene)-2,2-dimethyl-1,3-dioxane-4,6-dione, so that $R^1$ is (as in Example 9) $CH_2OCH_2CH_2OCH_3$, but n is 0.

The compound 53 is subsequently, as described in Example 9 (step 5), reacted with 31.6 g (160 mmol) of tosyl azide, 30.4 g (300 mmol) of triethylamine and 18.2 g (80 mmol) of 4-carboxyphenylsulfonyl azide to give the corresponding trifunctional α-diazo-β-keto ester

(54) of the formula I (n=0). The crude product is recrystallized from ethanol.

$C_{27}H_{38}N_6O_{15}$ calc.: C 47.23% H 5.58% N 12.24%
(MW 686.6) found: C 47.4% H 5.5% N 11.8%

As demonstrated in docket No. 16878/388, filed concurrently, photosensitive mixtures which contain the compound 54 of Example 73 as a photoactive component have bleach-out properties comparable to the compound of the formula I according to the invention, but the image-differentiating properties are not satisfactory.

What is claimed is:

1. A compound according to the formula I

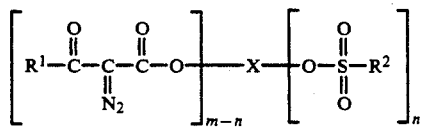

in which

R$^1$ and R$^2$ independently of one another are alkyl, cycloalkyl, aralkyl, aryl; or alkyl, cycloalkyl, aralkyl or aryl substituted by ($C_1$-$C_3$)-alkoxy, halogen, nitrile, amino, amido or nitro having 4 to 20 carbon atoms, or such groups wherein individual CH$_2$ groups are replaced by —O—, —S—, NR$_3$, —NH— or

groups,

X is an alkylene, cycloalkylene, arylene, heteroarylene, aralkylene; or alkylene, cycloalkylene, arylene, heteroarylene, or aralkylene substituted by ($C_1$-$C_3$) alkyl, ($C_1$-$C_3$) alkoxy, halogen, nitrile, amino or nitro having 2 to 22 carbon atoms, or such groups wherein individual —CH$_2$—groups are replaced by —O—, —S—, —NR$_3$—, —C(O)—O; —C(O)—NR$_3$—, —C(O)—NH—, —NR$_3$—C(O)—NR$_4$—, —O—C(O)NR$_3$—, —O—C-(O)—N— or —O— CO—O— groups, or such groups wherein CH groups are replaced by —N—, in which R$^3$ and R$^4$ independently of one another, are hydrogen or alkyl, aryl, aralkyl; or alkyl, aryl or aralkyl substituted by ($C_1$-$C_3$) alkyl, ($C_1$-$C_3$) alkoxy, halogen or amino, m is an integer from 3 to 8, n is an integer from 1 to 3, and m>n.

2. A compound as claimed in claim 1, wherein R$^3$ and R$^4$ are independently hydrogen or unsubstituted or substituted ($C_1$-$C_3$)alkyl, ($C_6$-$C_{12}$)aryl or ($C_6$-$C_{11}$)aralkyl.

3. A compound as claimed in claim 2, wherein R$^3$ and R$^4$ are independently hydrogen or ($C_1$-$C_3$)alkyl.

4. A compound as claimed in claim 2, wherein R$^3$ and R$^4$ are independently ($C_6$-$C_{12}$)aryl or ($C_6$-$C_{11}$)aralkyl which are unsubstituted or substituted on the rings thereof by ($C_1$-$C_3$)alkyl, ($C_1$-$C_3$)alkoxy, halogen or amino.

5. A compound as claimed in claim 4, wherein said halogen is chlorine or bromine.

6. A compound as claimed in claim 1, wherein at least one of R$^1$, R$^2$ and X is substituted by ($C_1$-$C_3$)alkyl, ($C_1$-$C_3$)alkoxy, halogen, amino or nitrile.

7. A compound as claimed in claim 6, wherein at least one of R$^1$, R$^2$ and X is substituted by ($C_1$-$C_3$)alkyl, or ($C_1$-$C_3$)alkoxy.

8. A compound as claimed in claim 1, wherein at least one of R$^1$ and R$^2$ is a substituted $C_4$-$C_{10}$-alkyl.

9. A compound as claimed in claim 8, wherein R$^1$ is a substituted aliphatic radical having 4 to 10 chain members.

10. A compound as claimed in claim 8, wherein in at least one of R$^1$ and R$^2$ up to 3 CH$_2$ groups are independently replaced by oxygen atoms, —NH— groups or keto groups.

11. A compound as claimed in claim 10, wherein R$^1$ is an alkyl in which up to two CH$_2$ groups are replaced by oxygen atoms.

12. A compound as claimed in claim 1, wherein R$^1$ is an unsubstituted alkyl containing up to 20 chain members.

13. A compound as claimed in claim 12, wherein R$^1$ is t-butyl.

14. A compound as claimed in claim 1, wherein at least one of R$^1$ and R$^2$ is unsubstituted or substituted cycloalkyl having 4, 5, 6 or 12 ring members.

15. A compound as claimed in claim 14, wherein said cycloalkyl has 4, 5 or 6 ring members.

16. A compound as claimed in claim 15, wherein said cycloalkyl has 6 ring members.

17. A compound as claimed in claim 14, wherein said cycloalkyl is unsubstituted.

18. A compound as claimed in claim 1, wherein at least one of R$^1$ and R$^2$ is an aralkyl radical having 2 to 11 chain members in the alkyl moiety of said radical.

19. A compound as claimed in claim 18, wherein said aralkyl radical has 2 to 5 chain members in the its alkyl parts.

20. A compound as claimed in claim 18, wherein said aralkyl has 1 or 2 chain members in its alkyl part.

21. A compound as claimed in claim 18, wherein in said aralkyl up to 3 CH$_2$ groups are replaced by an oxygen atom or a sulfur atom, with the proviso that at least one chain member is a carbon.

22. A compound ester as claimed in claim 21, wherein in the alkyl part of radical R$^1$ up to 2 CH$_2$ groups are replaced by heteroatoms and wherein said aralkyl contains 3 to 5 chain members.

23. A compound as claimed in claim 1, wherein R$^2$ is an unsubstituted alkyl containing 1 to 8 chain members.

24. A compound as claimed in claim 1, wherein R$^2$ is unsubstituted or substituted aryl or heteroaryl.

25. A compound as claimed in claim 24, wherein R$^2$ contains 6 to 12 carbon atoms.

26. A compound as claimed in claim 25, wherein R$^2$ is phenyl group.

27. A compound as claimed in claim 24, wherein R$^2$ is substituted with alkyl, alkoxy, halogen, nitrile, nitro, amino or amido.

28. A compound as claimed in claim 1, wherein up to 5 CH$_2$ groups in X are replaced by one of the replacement groups recited for X.

29. A compound as claimed in claim 1, wherein up to 3 CH$_2$ groups in X are replaced by one of the replacement groups recited for X.

30. A compound as claimed in claim 1, wherein X is and unsubstituted alkyl and has a maximum of 6 carbon atoms.

31. A compound as claimed in claim 30, wherein X contains a maximum of one C—C multiple bond.

32. A compound as claimed in claim 31, wherein X has 4 chain members.

33. A compound as claimed in claim 31, wherein X is trivalent.

34. A compound as claimed in claim 28, wherein said $CH_2$ groups are replaced by only oxygen atoms or only sulfur atoms.

35. A compound as claimed in claim 28, wherein a CH group has been replaced by

and no further substitution is present in the radical X.

36. A compound as claimed in claim 28, wherein X is cycloalkyl which is unsubstituted and which is adjacent to a $CH_2$ group of alkylene which is substituted by at least one of the replacement groups recited for X.

37. A compound as claimed in claim 36, wherein said cycloalkyl is directly adjacent to a nitrogen atom.

38. A compound as claimed in claim 37, wherein said cycloalkyl is directly adjacent to a nitrogen atom of the group

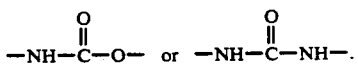

39. A compound as claimed in claim 36, wherein said cycloalkyl is linked to the oxygen atom of a

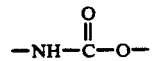

radical via an ethylene group.

40. A compound as claimed in claim 12, wherein X is an aralkyl in which the aromatic part thereof is linked to the alkylene part thereof via a sulfur atom or an oxygen atom.

41. A compound as claimed in claim 40, wherein said aromatic part is a phenyl or phenylene.

42. A compound as claimed in claim 1, wherein m is an integer from 3 to 6, and n is 1 or 2.

* * * * *